(12) United States Patent
Kolpashchikov

(10) Patent No.: US 8,354,227 B2
(45) Date of Patent: Jan. 15, 2013

(54) BINARY DEOXYRIBOZYME PROBES FOR NUCLEIC ACID ANALYSIS

(75) Inventor: Dmitry Kolpashchikov, New York, NY (US)

(73) Assignee: Columbia University in the City of New York, New York City, NY (US)

( * ) Notice: Subject to any disclaimer, the term of this patent is extended or adjusted under 35 U.S.C. 154(b) by 848 days.

(21) Appl. No.: 12/162,605

(22) PCT Filed: Feb. 4, 2007

(86) PCT No.: PCT/US2007/061583
§ 371 (c)(1),
(2), (4) Date: Jul. 29, 2008

(87) PCT Pub. No.: WO2008/054834
PCT Pub. Date: May 8, 2008

(65) Prior Publication Data
US 2010/0015608 A1    Jan. 21, 2010

Related U.S. Application Data

(60) Provisional application No. 60/764,924, filed on Feb. 3, 2006.

(51) Int. Cl.
| | | |
|---|---|---|
| C12Q 1/68 | (2006.01) | |
| C07H 21/00 | (2006.01) | |
| C07H 21/02 | (2006.01) | |
| C07H 21/04 | (2006.01) | |

(52) U.S. Cl. ....... 435/6.1; 435/22.1; 435/23.1; 435/24.3
(58) Field of Classification Search ............... 435/6, 6.1; 536/23.1, 24.3
See application file for complete search history.

(56) References Cited

U.S. PATENT DOCUMENTS

| | | | |
|---|---|---|---|
| 6,413,722 | B1 | 7/2002 | Arnold et al. |
| 6,706,474 | B1 * | 3/2004 | Lu et al. ............... 435/6 |
| 2002/0102694 | A1 * | 8/2002 | Breaker et al. ......... 435/199 |
| 2002/0127574 | A1 * | 9/2002 | Mirkin et al. .......... 435/6 |
| 2002/0172960 | A1 | 11/2002 | Bao et al. |
| 2004/0070426 | A1 * | 4/2004 | Stojanovic ............ 326/136 |
| 2004/0161778 | A1 * | 8/2004 | Lu et al. ............... 435/6 |
| 2005/0233455 | A1 * | 10/2005 | Damha et al. .......... 435/455 |
| 2007/0231810 | A1 | 10/2007 | Todd et al. |

FOREIGN PATENT DOCUMENTS

| | | |
|---|---|---|
| EP | 1063296 * | 12/2000 |
| WO | 92/20823 A1 | 11/1992 |
| WO | WO 0040751 A2 | 7/2000 |
| WO | WO/2007/041774 A1 | 4/2007 |
| WO | WO/2007/065926 A1 | 6/2007 |
| WO | WO 2007/115242 A2 | 10/2007 |
| WO | WO/2008/040095 A1 | 4/2008 |
| WO | 2008/054834 A2 | 5/2008 |
| WO | 2010/059944 A1 | 5/2010 |

OTHER PUBLICATIONS

Breaker and Joyc. A DNA wnzyme wiMd2+-dependent RNA phosphoesterase activity. Chamistry & Biology 2: 655-660 (1995).*
The Stratagene Catalog p. 39 (1988).*
Bichenkova, E. et al., Target-assembled tandem oligonucleotide systems based on exciplexes for detecting DNCA mismatches and single nucleotide polymorphisms, journal, May 2005, pp. 956-964, Elsevier.
Li, Q., A new class of homogeneous nucleic acid probes based on specific displacement hybridization, journal, Aug. 2001, pp. 1-9, vol. 30, No. 2, Oxford University Press.
Supplementary European Search Report, Application Number: 07759922.3-1222/2013561, Nov. 23, 2009.
International Search Report and Written Opinion, PCT/US 09/65341, Nov. 20, 2009, pp. 1-10.
Kolpashchikov, D., Split DNA Enzyme for Visual Single Nucleotide Polymorphism Typing, journal, Jacs Communication, Dec. 17, 2007, pp. 2934-2935, vol. 130, No. 10, American Chemical Society, United States.
Kolpashchikov, Dmitry M., "A Binary DNA Probe for Highly Specific Nucleic Acid Recognition", J. Am. Chem. Soc., vol. 128, No. 32, Jul. 21, 2006, 128, pp. 10625-10628.
International Search Report and Written Opinion for PCT/US07/61583, dated Sep. 26, 2008, pp. 1-12.
International Search Report and Written Opinion for PCT/US07/65744, dated Sep. 2, 2008, pp. 1-11.
Muller., IEE Proc Nannobiotechnology, Apr. 2006, vol. 153, No. 2, 31-40.
Amontov, et al., J. Am. Chem. Society, 1996, vol. 118, 1624-28.
Wang, et al., J. Mol. Biol. 2001, vol. 301-, 723-34.
Todd AV, et al. May 2000; 46(5):593-4).
Macdonald J, et al. Methods Mol Biol. 2006;335:343-63.
Kolpashchikov D.M., Stojanovic M.N. (2005) "Boolean control of aptameric binding states." JACS, 127, 11348-11341.
Kolpashchikov D.M. (2005) Binary malachite green aptamer for fluorescent detection of nucleic acids. JACS, 127, 12442-12443.
Tyagi,S., et al.. (1996) Nat. Biotechnol. 14, 303-308; 15.
Levy, M., Ellington, A. D. 2003 Proc Natl Acad Sci U S A. 100:6416-6421.
Marras,S.A., et al. (2006) Clin. Chim. Acta. 363, 48-60.
Bonnet,G., et al. (1999) Proc. Natl. Acad. Sci. U. S. A. 96, 6171-6176
Tyrrell, J. V. and Bergquist, P. R. New Zealand Journal of Marine and Freshwater Research, 1997, vol. 31:551-560.
Babendure et al., "Aptanners Switch on Fluorescence of Triphenylmethane Dyes", "J. Am. Chem. Soc.", Nov. 8, 2003, pp. 14716-14717, vol. 125, Publisher: American Chemical Society, Published in: US.
Sando et al., "Light-Up HoechstDNA AptamerPair: Generation of an Aptamer-Selective Fluorophore from a Conventional DNA-Staining Dye", "ChemBioChem", 2007, pp. 1795-1803, vol. 8, Publisher: Wiley-VCH Verlag GmbH & Co., Published in: Germany.

(Continued)

Primary Examiner — Ethan C Whisenant
(74) Attorney, Agent, or Firm — Evans & Molinelli PLLC; Judith A. Evans

(57) ABSTRACT

New binary deoxyribozyme or ribozyme probes and methods are described for nucleic acid analysis, which allows the detection of nucleic acids under mild physiologic conditions with extraordinary specificity and high sensitivity to single nucleotide mismatches without PCR amplification.

32 Claims, 10 Drawing Sheets

OTHER PUBLICATIONS

ISA, "International Search Report and Written Opinion for Corresponding International Application No. PCT/US10/22428", Mar. 19, 2010, pp. 1-12, Published in: US.

ISA, "International Preliminary Report on Patentability for Corresponding International Application No. PCT/US2010/022428", Aug. 2, 2011, pp. 1-8, Published in: Switzerland.

Kolpashchikov, Dmitry M., "A Binary Deoxyribozyme for Nucleic Acid Analysis", "ChemBioChem", 2007, pp. 2039-2042, vol. 8, Publisher: Wiley-VCH Verlag GmbH & Co., Published in: Germany.

Mokany et al., "MNAzymes, a Versatile New Class of Nucleic Acid Enzymes That Can Function as Biosensors and Molecular Switches", "J. Am. Chem. Soc.", 2010, pp. 1051-1059, vol. 132, No. 3, Publisher: American Chemical Society.

Deng, M. et al., "Highly Effective Colormetric and Visual Detection of Nucleic Acids Using an Asymmetrically Split Peroxidase DNAzyme", J. Am. Chem. Soc., 2008, v.130 (39), pp. 13095-13102. American Chemical Society. http://pubs.acs.org/doi/abs/10.1021/ja803507d.

Xiao, Y. et al., "Lighting Up Biochemiluminescence by the Surface Self-Assembly of DNA-Hemin Complexes", ChemBioChem, 2004, v.5, (3), pp. 374-379. http://onlinelibrary.wiley.com/doi/10.1002/cbic.200300794/abstract.

Travasico, P., et al., "A ribozyme and a catalytic DNA with peroxidase activity: active sites versus cofactor-binding sites", Chemistry & Biology, 1999, v. 6 (11), pp. 779-787. Canada. XP55036481 http://www.cell.com/chemistry-biology/abstract/S1074-5521%2899%2980125-2.

Supplementary European Search Report and Written Opinion for EP 09828292. European Patent Office. Munich, Germany, pp. 1-9. Sep. 5, 2012.

* cited by examiner

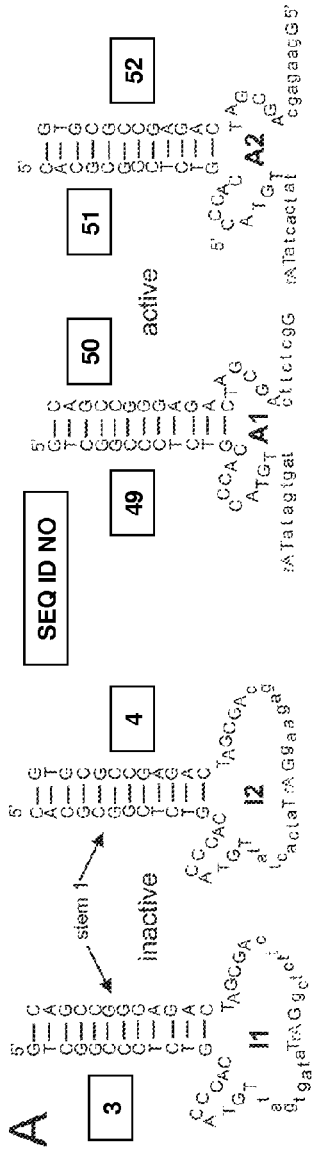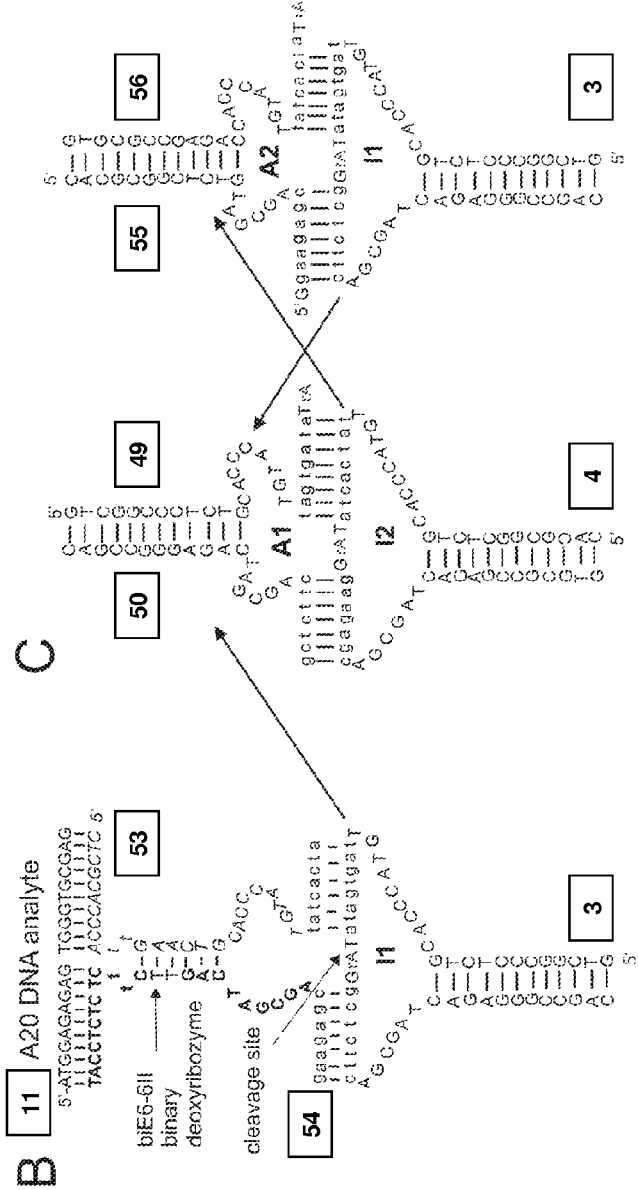
FIG. 5

A61 [SEQ ID NO]

5'-GTAAAGCCAACTTTAGTTGGGGAGGAAAGCCCT CAAGGTTAATAGCCCTTGGGGAGGAGGACGTTAC

[63]

biE6-25

```
CGTGA AATCAACCCCTCCTTTCGGA          GTTCCAATTATCGGAACCCCCTCCT-5'
                       ↑            ↑                           [65]
             25 nt analyte binding arms
                            t   t G                    t G
                          t C                         A
                          T                           A
                         G                             C
                         A                             T
                         C                             G
                            A   G                    C A C C
                                 T                         C
                           [64]  G  C                      T A
                                 5'-CTCTTC               TAGTGA
```

BINARY DEOXYRIBOZYME PROBES FOR NUCLEIC ACID ANALYSIS

CROSS REFERENCE TO RELATED APPLICATIONS

This application claims benefit of Provisional Application 60/764,924, filed on Feb. 3, 2006, incorporated herein by reference, under 35 U.S.C. §119(e).

STATEMENT OF GOVERNMENTAL INTEREST

This research was made with US government support under NIH NHGRI R21 HG004060, NIBIB, R01 EB000675, and NSF, BES 0321972. The Government has certain rights in the invention.

BACKGROUND OF THE INVENTION

1. Field of the Invention

The present invention relates to binary deoxyribozyme probes for nucleic acid analysis.

2. Description of the Related Art

The growing importance of sensitive and selective determination of nucleic acids is associated with detection of viruses, microorganisms, and genetic traits that are not only of clinical significance, but also of environmental, defense, veterinary and agricultural importance. Simple and sensitive sequence-specific methods of nucleic acid analysis are needed, for example, for the rapid diagnosis of infection and genetic diseases, genome study, mRNA monitoring in living cells, and for environmental forensic applications. Most of these methods require PCR amplification of the genetic material prior to its analysis. While PCR represents the ultimate in terms of sensitivity, it has significant drawbacks including complexity, sensitivity to contamination, cost, lack of portability, and major challenges with respect to multiplexing. Therefore there is still a need for new straightforward, inexpensive, highly selective and highly sensitive methods for nucleic acid analysis.

SUMMARY OF THE INVENTION

Certain aspects of the invention are directed to binary deoxy- or ribozyme probes for nucleic acid analysis that are highly selective and sensitive. In one of the embodiments the non-naturally occurring binary deoxyribozyme or ribozyme probe for detecting a nucleic acid analyte, is made of two antiparallel oligonucleotide strands, wherein the first oligodeoxyribonucleotide strand includes:
   a. at its 5'-terminus a substrate binding arm that is complementary to and hybridizes to a substrate,
   b. a catalytic core that flanks the substrate binding arm,
   c. a probe binding arm that flanks the catalytic core, which probe binding arm is complementary to and hybridizes to a corresponding probe binding arm on the second strand when the first and second strands of the probe are bound to the analyte,
   d. a linker sequence that flanks the probe binding arm, and
   e. at its 3'-terminus an analyte binding arm that flanks the linker sequence, which analyte binding arm is complementary to part of the analyte and hybridizes to the analyte.

The second oligodeoxyribonucleotide strand has the same elements in antiparallel direction. In other embodiments the probes also have a structure stabilization arm at the 3' terminus flanking the analyte binding arm on the first strand, which structure stabilization arm is complementary to and hybridizes to another nucleotide sequence in the first probe strand. The second strand also has the structure stabilization arm but on the other end of the molecule. The length and sequence of the various components of the probe can be varied as is described below to customize the probe for a particular analyte and optimize the reactions.

In another aspect the invention provides for various assays to detect analyte in a sample. In one embodiment, the assay having the steps of: 1. forming a mixture that includes a. a binary deoxyribozyme (or ribozyme) probe comprising an analyte binding arm that is complementary to and hybridizes to all or part of the known nucleotide sequence in the analyte, and further comprising a substrate binding arm that binds to and cleaves a first inactive cross-catalytic deoxyribozymogen thereby forming a first active deoxyribozyme; b. a first inactive cross-catalytic deoxyribozymogen, that hybridizes to the first substrate binding arm and is thereby cleaved to generate a first activated deoxyribozyme (or ribozyme) that is capable of hybridizing with both a reporter substrate and a second inactive cross-catalytic deoxyribozymogen; c. a second inactive cross-catalytic deoxyribozymogen that hybridizes to the first active deoxyribozyme and is thereby cleaved to generate a second active deoxyribozyme that, in turn, hybridizes to and cleaves the first inactive cross-catalytic deoxyribozymogen, thereby generating the first active deoxyribozyme, and d. a reporter substrate that hybridizes to and is cleaved by the first active deoxyribozyme to generate signal products that can be detected; 2. adding to the mixture DNA or RNA analyte and incubating the mixture under conditions that permit nucleic acid hybridization, 3. determining if the reporter substrate has been cleaved by detecting signal products in the mixture, and 4. if signal products are detected, concluding that the DNA or RNA analyte was present in the sample.

Certain other embodiments are directed to truncated versions of the binary probe that permit the use to customize the probe by adding analyte binding arms as required. Certain truncated versions of the binary probe also permit the user to customize the substrate binding arm. Other aspects of the invention are directed to certain binary deoxyribozyme probes: biE6-10, biE6-10h, biE6-6II, I1, I2, A1, and A2. Other aspects of the invention are directed to various assays that detect the presence of analyte in a sample. In one assay to detect an RNA or DNA analyte having a known nucleotide sequence in a sample using a non-naturally occurring binary deoxyribozyme probe, the steps include:
   a) providing a binary deoxyribozyme probe comprising a nucleotide sequence that is complementary to and hybridizes to all or part of the known nucleotide sequence in the analyte, thereby activating the probe,
   b) providing a substrate that hybridizes to and is cleaved by the probe, which cleavage produces one or more signal products that can be detected,
   c) creating a mixture comprising the sample, the binary probe and the substrate,
   d) maintaining the mixture of step b) for a sufficient period of time and under reaction conditions that allow the analyte to hybridize to the complementary nucleotide sequence in the probe, thereby activating the probe which causes cleavage of the substrate, and
   e) determining that the analyte is present in the sample if the one or more signal products are detected. The same basic assay can be done using binary ribozyme probes.

In another assay, a cascade is used to amplify the signal. In an embodiment of such an assay for detecting a DNA or RNA analyte in a sample comprising a known nucleotide sequence, the assay has the steps of:

1. forming a mixture comprising:
   a. a non-naturally occurring binary deoxyribozyme probe comprising an analyte binding arm that is complementary to and hybridizes to all or part of the known nucleotide sequence in the analyte, and further comprising a substrate binding arm that binds to and cleaves a first inactive cross-catalytic deoxyribozymogen thereby forming a first active deoxyribozyme;
   b. a first inactive cross-catalytic deoxyribozymogen, that hybridizes to the substrate binding arm on the probe and is thereby cleaved to generate a first activated deoxyribozyme that is capable of hybridizing with both a reporter substrate and a second inactive cross-catalytic deoxyribozymogen, and
   c. a second inactive cross-catalytic deoxyribozymogen that hybridizes to the first active deoxyribozyme and is thereby cleaved to generate a second active deoxyribozyme that, in turn, hybridizes to and cleaves the first inactive cross-catalytic deoxyribozymogen, thereby generating the first active deoxyribozyme, and
   d. a reporter substrate that hybridizes to and is cleaved by the first active deoxyribozyme to generate signal products that can be detected;
2. adding to the mixture DNA or RNA analyte and incubating the mixture under conditions that permit nucleic acid hybridization,
3. determining if the reporter substrate has been cleaved by detecting signal products in the mixture, and
4. if signal products are detected, concluding that the DNA or RNA analyte was present in the sample.

BRIEF DESCRIPTION OF THE DRAWINGS

The present invention is illustrated by way of example, and not by way of limitation, in the figures of the accompanying drawings and in which like reference numerals refer to similar elements.

FIG. 6 Optical detection of deoxyribozyme activity using oligonucleotide-immobilized nanoparticles. A: recognition of circular Substrate S by the deoxyribozyme A1; B: linear oligonucleotide L. C: Colloidal mixture of two species of the oligonucleotide-immobilized gold nanoparticles. D: Aggregation of gold nanoparticles triggered by oligonucleotide L.

DEFINITIONS

Figure 1:
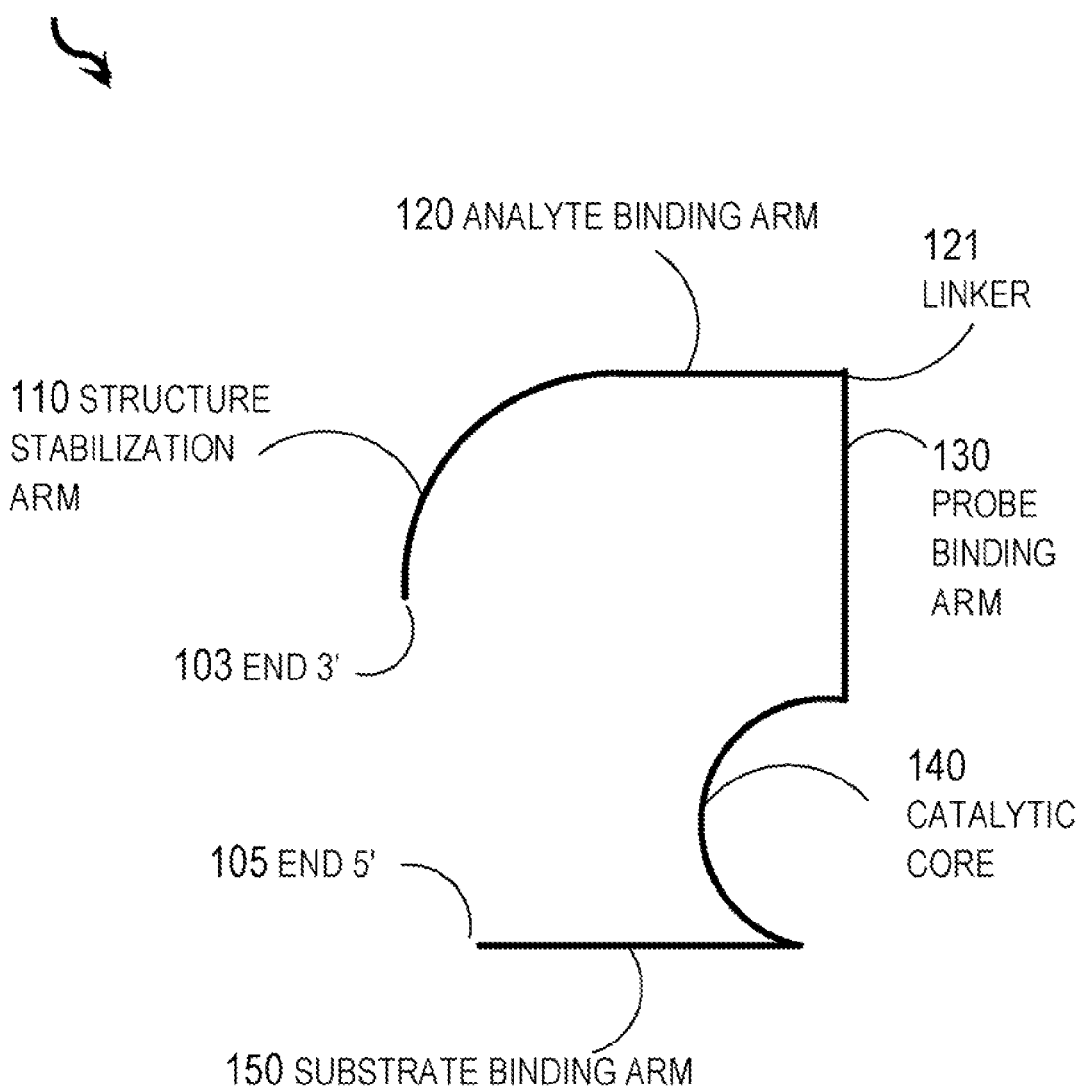
FIG. 1 A diagram of the first strand of a binary probe.

As used herein, the terms "deoxyribozyme" and "ribozyme" are used to describe a DNA or RNA-containing nucleic acid that is capable of functioning as an enzyme. In the present disclosure, the term "deoxyribozyme" and "ribozyme" includes endoribonucleases and endodeoxyribonucleases, although deoxyribozymes/ribozymes with endoribonuclease activity are particularly preferred. Other terms used interchangeably with deoxyribozyme/ribozyme herein are "enzymatic DNA/RNA molecule", "DNAzyme/RNAzyme", or "catalytic DNA/RNA molecule", which terms should all be understood to include enzymatically active portions thereof, whether they are produced synthetically or derived from organisms or other sources.

The term "enzymatic DNA/RNA molecules" also includes DNA/RNA molecules that have complementarity in a substrate-binding region to a specified oligonucleotide target or substrate; such molecules also have an enzymatic activity which is active to specifically cleave the oligonucleotide substrate. Stated in another fashion, the enzymatic DNA/RNA molecule is capable of cleaving the oligonucleotide substrate intermolecularly. This complementarity functions to allow sufficient hybridization of the enzymatic DNA/RNA molecule to the substrate oligonucleotide to allow the intermolecular cleavage of the substrate to occur.

As used herein, the term "base pair" (bp) is generally used to describe a partnership of adenine (A) with thymine (T) or uracil (U), or of cytosine (C) with guanine (G), although it should be appreciated that less-common analogs of the bases A, T, C, and G (as well as U) may occasionally participate in base pairings. Nucleotides that normally pair up when DNA or RNA adopts a double stranded configuration may also be referred to herein as "complementary bases".

"Complementary nucleotide sequence" here generally refers to a sequence of nucleotides in a single-stranded molecule or segment of DNA or RNA that is sufficiently complementary to that on another single oligonucleotide strand to specifically hybridize to it with consequent hydrogen bonding. Where single nucleotide polymorphisms are the target for detection, then the complementarity between the analyte and analyte binding arm on the binary probes should be exact, 100%. If less selectivity is required, then routine experimentation will determine the level of complementarity that provides the desired result.

"Nucleotide" generally refers to a monomeric unit of DNA or RNA consisting of a sugar moiety (pentose), a phosphate group, and a nitrogenous heterocyclic base. The base is linked to the sugar moiety via the glycosidic carbon (1' carbon of the pentose) and that combination of base and sugar is a "nucleoside". When the nucleoside contains a phosphate group bonded to the 3' or 5' position of the pentose, it is referred to as a nucleotide. A sequence of nucleotides is typically referred to herein as a "base sequence" or "nucleotide sequence", and their grammatical equivalents, and is represented herein by a formula whose left to right orientation is in the conventional direction of 5'-terminus to 3'-terminus, unless otherwise specified.

"Nucleotide analog" generally refers to a purine or pyrimidine nucleotide that differs structurally from A, T, G, C, or U, but is sufficiently similar to substitute for the normal nucleotide in a nucleic acid molecule. As used herein, the term "nucleotide analog" encompasses altered bases, different or unusual sugars (i.e. sugars other than the "usual" pentose), or a combination of the two. Nucleotide analogs of DNA or RNA can be used to make binary probes. Examples of nucleotide analogs useful according to the present invention include those listed in the approved listing of modified bases at 37 CFR .sctn.1.822 (which is incorporated herein by reference). Other useful analogs include those described in published international application no. WO 92/20823 (the disclosures of which are incorporated herein by reference), or analogs made according to the methods disclosed therein.

"Oligonucleotide or polynucleotide" generally refers to a polymer of single-stranded nucleotides. As used herein, "oligonucleotide" and its grammatical equivalents will include the full range of nucleic acids. An oligonucleotide will typically refer to a nucleic acid molecule comprised of a linear strand of deoxy- and ribonucleotides.

In various embodiments, the binary deoxyribozyme probe of the present invention may combine one or more modifications or mutations including additions, deletions, and substitutions. These mutations may, for example, change the length of, or alter the nucleotide sequence of, a loop, a spacer region or a recognition sequence (or domain). Modification or mutation of the recognition site via well-known methods allows one to alter the sequence specificity of an enzymatic nucleic acid molecule.

As used herein, the term "physiologic conditions" is meant to suggest reaction conditions emulating those found in mammalian organisms, particularly humans. While variables such as temperature, availability of cations, and pH ranges may vary as described in greater detail below, "physiologic conditions" generally comprise a temperature of about 35 40° C., with 37° C. being particularly preferred, as well as a pH of about 7.0 8.0, with 7.5 being particularly preferred, and further comprise the availability of cations, preferably divalent and/or monovalent cations, with a concentration of about 2 15 mM $Mg^{2+}$ and 0 1.0 M $Na^+$ being particularly preferred

DETAILED DESCRIPTION

New binary deoxyribozyme or ribozyme probes and methods are described for nucleic acid analysis, which allows the detection of nucleic acids under mild physiologic conditions with extraordinary specificity and high sensitivity to single nucleotide mismatches without PCR amplification. For example, a blood sample can be treated at room temperature in the buffer compatible with the binary deoxyribozyme probe at near physiologic conditions to detect viral RNA or mRNA produced by cancer cells. The newly discovered binary deoxyribozyme and ribozyme probes ("the binary probe") have two separate, antiparallel DNA or RNA strands, respectively. The basic probe has several distinct regions on each strand: an analyte binding arm, a probe binding arm, a catalytic core, and a substrate binding arm that binds to a fluorescent or other reporter substrates indicating that the analyte has been detected. In the absence of a nucleic acid analyte, the strands are dissociated and the deoxyribozyme or ribozyme is inactive. Addition of a specific DNA/RNA analyte, some or all of which is complementary to the respective analyte binding arms on the two halves of the probe, results in hybridization of the analyte binding arms to the corresponding complementary nucleotides on the analyte. When the analyte binds to probe, the deoxyribozyme or ribozyme catalytic core reforms thereby activating the deoxyribozyme. When the deoxyribozyme is activated it binds through the substrate binding arms to a substrate and cleaves it, thereby generating a signal that the analyte has been detected. In the preferred embodiment the substrate fluoresces on cleavage. Certain other embodiments include various kits that include the binary deoxyribozyme or ribozyme probe customized to bind to a nucleic acid analyte of interest, and the substrate for the enzyme. These probes can be used to detect clinically significant nucleic acids such as those indicating a viral or bacterial infection.

In the following description, for the purposes of explanation, numerous specific details are set forth in order to provide a thorough understanding of the present invention. It will be apparent, however, to one skilled in the art that the present invention may be practiced without these specific details.

Binary Deoxyribozyme and Ribozyme Probes: Structure and Function

Deoxyribozymes or DNA enzymes are catalytic DNA oligonucleotides derived by in vitro selection (Joyce G F (2004) Annu. Rev. Biochem., 73 791-836; Piunno, P. A., Krull, U. J. 2005. Trends Anal. Bioanal. Chem. 381:1004-1011; incorporated herein by reference.) They have been used for site-specific mRNA cleavage (Schubert S, et al. Curr Drug Targets. 2004 November;5(8):667-81), and other biotechnological applications such as nucleic acid quantification (Todd A V, et al. Clin Chem. 2000 May;46(5):593-4), calorimetric $Pb^{2+}$ detection (Liu J., JACS 2004, 126, 12298-12305), molecular Boolean computation (Macdonald J, et al. Methods Mol Biol. 2006;335:343-63, Kolpashchikov D. M., et al. Journal of the American Chemical Society, 127, 11348-11341) and others (reviewed in Silverman S K Nucleic Acids Res. Nov. 11, 2005;33(19):6151-63, all references are incorporated herein by reference). The advantages offered by catalytic DNAs and RNAs include high chemical stability, low cost for synthesis, ease of structural prediction and modification and biocompatibility. The binary probes of the present invention, all of which are exemplified by deoxyribozyme probes here, can be used to detect very small RNAs that cannot be detected at the present time with PCR. Deoxyribozyme probes can detect either DNA or RNA analytes. In various embodiments, the nucleic acid analyte comprises RNA, modified RNA, DNA, modified DNA, one or more nucleotide analogs, or composites of any of the foregoing. Binary probes (deoxy- and ribozyme probes) of the present invention may be prepared or engineered using any method known in the art, including methods such as those of preparing enzymatic DNA molecules that are described in the art. Methods of altering the length of the DNA or RNA nucleotides are known in the art and include enzymatic or chemical synthesis of RNA and DNA nucleotides. Chemical synthesis is the most efficient way to make small binary probes, and it can be performed using an Applied Biosystems (Foster City, Calif.) oligonucleotide synthesizer according to the manufacturer's instructions.

Conventional techniques for nucleic acid analysis use buffers with low ionic strength, denaturing agents (formamide) or elevated temperatures (usually 50-60° C.) with precise temperature control, and do not reliably detect single nucleotide polymorphisms, especially if a mismatch is located at the ultimate or penultimate position of the probe-analyte hybrid (Urakawa, H., et al. Appl. Environ. Microbiol. 2003, 69, 2848-2856.). One approach to enhance selectivity of nucleic acid hybridization was realized by making conformationally constrained probes such as molecular beacons (MBs) (Tyagi, S., et al. (1996) Nat. Biotechnol. 14, 303-308; 15; Bonnet, G., et al. (1999) Proc. Natl. Acad. Sci. U.S.A. 96, 6171-6176; Marras, S. A., et al. (2006) Clin. Chim. Acta. 363, 48-60, incorporated herein by reference). MBs are monolithic oligodeoxyribonucleotide hairpins with a fluorophore and a quencher conjugated to opposite ends of the oligonucleotide. When bound to a complementary nucleic acid, the MB switches to an elongated conformation that increases their fluorescence. MBs distinguish mismatches over a wider temperature range than unstructured probes, however, MBs are not sensitive to single base mismatches and they are relatively expensive.

The new binary probes of the present invention depicted in FIG. 1 are less expensive to make, more sensitive and highly selective. They reliably detect single nucleotide polymorphisms in analytes of up to about 20 nucleotides in length. In one embodiment, the binary deoxyribozyme or ribozyme probes have a basic structure that includes on each oligonucleotide strand a substrate binding arm (150) (that binds the enzyme substrate such as a fluorescent substrate), half of the catalytic core of the enzyme (140), a probe binding arm (130), a linker (121) joining the probe binding arm to the analyte binding arm (120), and the analyte binding arm. FIG. 1 Optional embodiments include structure stabilization arms (110). Certain embodiments are directed to deoxyribozyme or ribozyme probes having this basic structure. The two strands of the binary probe are antiparallel. In the presence of a specific nucleic acid analyte the two DNA strands of the probe hybridize to the abutting complementary nucleotides of the target analyte, or the targeted sequences in analyte that can be much longer than the combined length to the analyte binding arms on the probe. When this happens, the probe binding arms of the two strands hybridize and reform the catalytically active core. The active enzyme then binds to and cleaves a reporter substrate, such as a fluorophore and quencher, thereby generating a signal that the analyte has been detected. The new binary probes are highly selective, consistently recognizing single nucleotide substitutions or mismatches in a 20-mer section of a target DNA or RNA analyte at room temperature under near physiologic conditions. Moreover, they are highly sensitive and report the presence of DNA/RNA analyte in just 1 picoMole amounts. As will be discussed below, various truncated forms of the probe are also contemplated by the present invention that enables users to obtain a kit and make their own customized probes.

For optimum selectivity, for example of SNPS, the analyte analyte binding arm of each strand of the probe should be no longer than about 10 nucleotides long. There is no need for longer analyte binding arms because a length of 20 nucleotides will cover any unique sequence in the genome. Elongated analyte binding arms (for example up to about 25 nucleotides) are more sensitive and may be used when the primary objective is high sensitivity, for example, in a sample with an extremely low analyte concentration. However, the increase in sensitivity was not statistically significant. FIG. 7. It is important to note, however, that the analyte itself can be of any length from 14 to many thousand nucleotides. The hybrids of the binary probes of the present invention are substantially destabilized by a single mismatched base pair, thereby preventing cleavage of the substrate and detection of the mismatched analyte. The binary probes thus provide an extraordinary level of selectivity.

The new probes and analytic methods using them have the following major advantages:

1) Unprecedented high selectivity: the probes and methods permit reliable discrimination of a single base substitution at any position of a 14-20 nucleotide length or target in a DNA/RNA analyte.

2) High sensitivity: potentially a single nucleic acid molecule can be detected without PCR amplification.

3) Mild reaction conditions: the method will work in buffers close to physiological conditions and at room temperature, thus being potentially applicable in living cells.

4) Relatively lower costs. The new deoxyribozyme/ribozyme probes enable the specific and sensitive nucleic acid analysis and are relative cheap to make.

Figure 2:
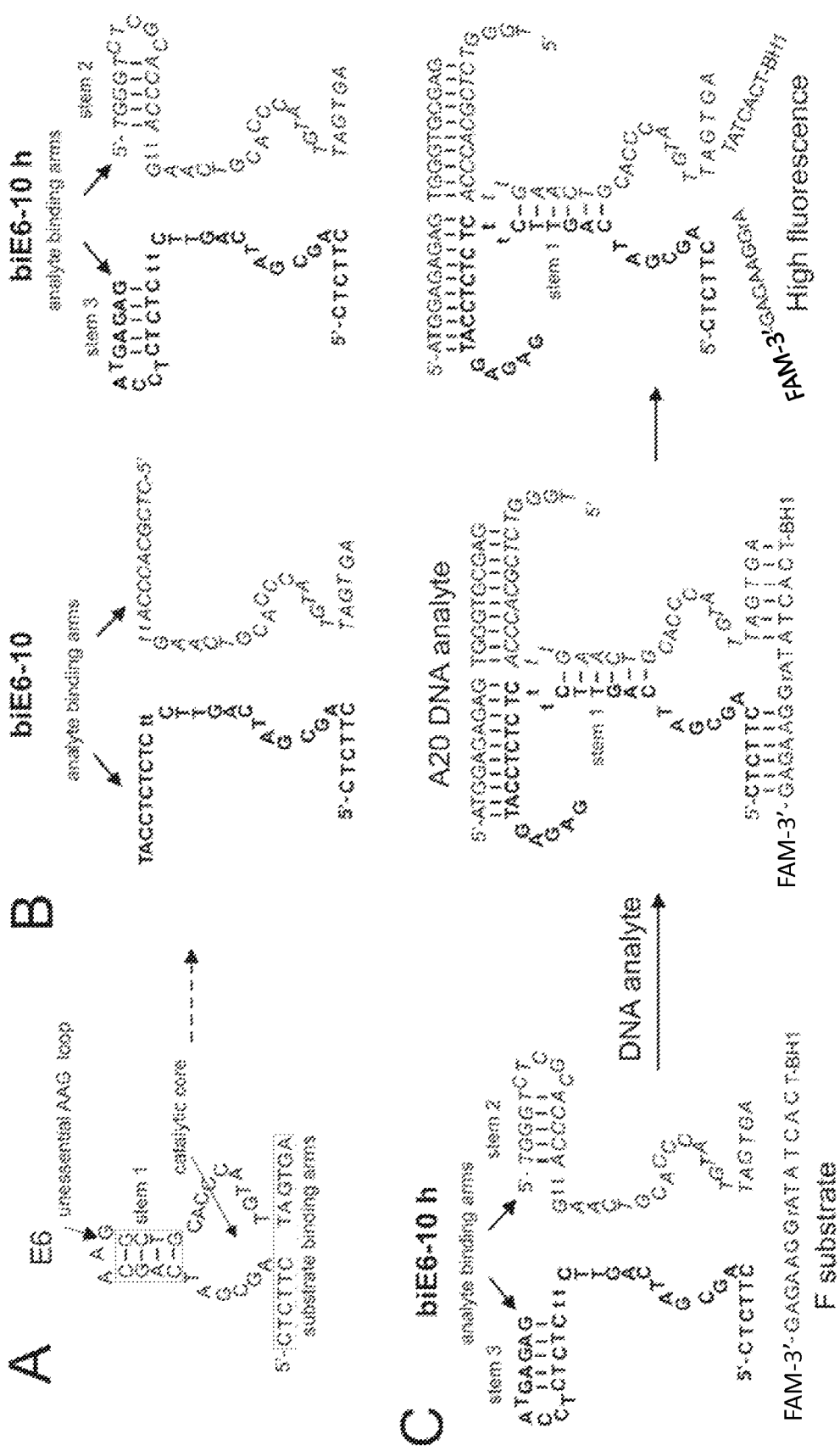
FIG. 2 A: Parent deoxyribozyme E6. B: Binary deoxyribozyme. C: Binary deoxyribozyme probe biE6-10 and biE6-10h showing stem-loop structures; BiE6-10h binds to DNA analyte A20 (20 nucleotides long) and Substrate F, reconstituted catalytic core cleaves Substrate F.
Figure 3:
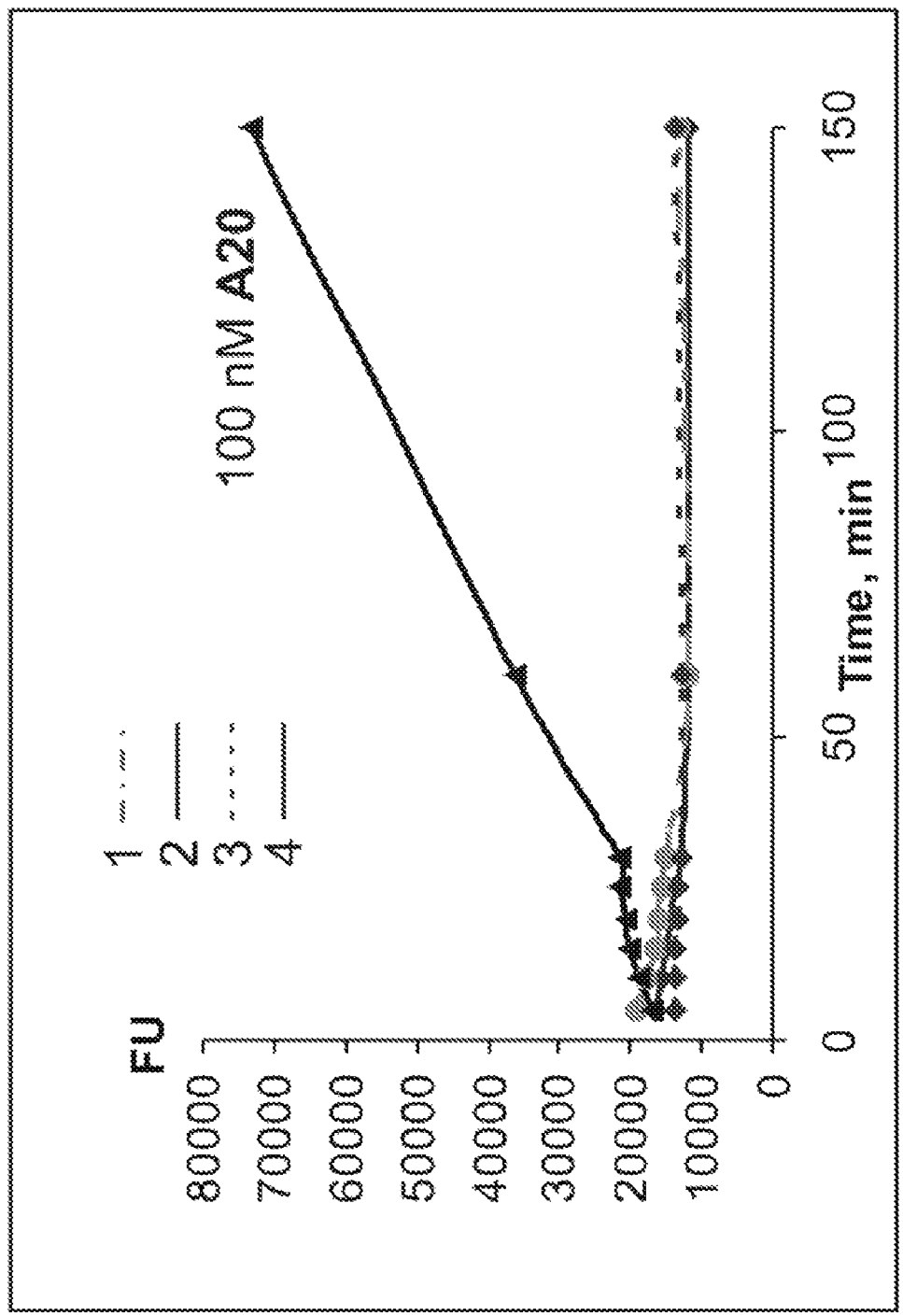
FIG. 3. Fluorescent substrate F and biE6-10h incubated in the absence (line 2) or presence (line 3) of analyte A20 DNA. pH 7.4, room temperature. Fluorescent intensities at 517 nm are represented as functions of the incubation time. Line1 F substrate alone.

Several of the new binary deoxyribozyme probes of the present invention were modified from a parent E6 deoxyribozyme described by others, and are depicted in FIG. 2. E6 was made by Breaker and Joyce by artificial selection and rational design (Breaker, R. R., Joyce, G. F. 1995 Chem Biol. 2:655-660, incorporated herein by reference). Because E6 is a DNA enzyme it is much cheaper to synthesize and is more stable to degradation than its RNA counterpart. Deoxyribozyme binary probes are generally preferred for this reason. The phosphodiester bond cleavage activity of E6 approaches that observed for the hammerhead ribozyme. Maxizyme and hammerhead ribozyme as well as other ribozymes including X-motif, MR2 ribozyme and C1V2 trans-ribozyme have structures that can be modified to make the new binary ribozyme probes as described. (Schubert S, et al. Curr Drug Targets. 2004 November; 5(8): 667-81; Lazarev D, et al., RNA 2003, June; 9(6):688-97; Breaker R R et al. RNA 2003 August:9(8): 949-57, incorporated herein by reference). Other enzymes that can be adapted to make binary probes according to the present invention include the 8-17 deoxyribozyme, (Santoro S W, Joyce G F. 1997 PNASUSA Vol. 94, 4262-4266) and pH6DZ1 deoxyribozyme, and other high-branching deoxyribozymes (Lu, Y.; et al. 2003 Biosens Bioelectron. 18:529-54, these references are incorporated herein by reference). The binary probes of the present invention can be made using the catalytic core of any known deoxyribozyme or ribozyme that contains a variable stem-loop configuration.

To make the new probe called biE6-10, we divided E6 into two halves, removed the unessential AAG loop, and added analyte binding arms to the ends of each of the two halves via di-thymidine linkers (FIGS. 2A and 2B). One embodiment of the invention is directed to biE6-10 without analyte binding arms, having the advantage that users can customize the probe with any analyte binding arm they choose, and to biE6-10 having analyte binding arms that hybridize with and are complementary to a known analyte or region of a known region of a known analyte. To make another version of the probe called biE6-10h (FIG. 2B), we added pentanucleotide fragments at the ends of each analyte binding arm called "structure stabilization arms" (FIG. 1, callout no. 110). Structure stabilization arms allow stem-loop formation that enhances selectivity of the probe by preventing the dissociated halves of the probe from binding with one another until the analyte binding arms (120) have bound to the analyte. The analyte binding arms of biE6-10 and biE6-10h were designed specifically to bind to the test analyte A20, however it is important to emphasize that the length and nucleic acid sequence in the analyte bindings arms is customized to the particular analyte being assayed, and the specificity required. One embodiment of the invention is directed to the bE6-10h probe shown in FIG. 2B without analyte binding arms, allowing users to customize the analyte binding arms.

When the nucleic acid analyte is added, the two parts of the enzyme probe cooperatively hybridize to the complementary regions of the analyte, causing the probe binding arms to hybridize with one another (designated "stem 1" in FIG. 2, and FIG. 4), thereby reforming the deoxyribozyme catalytic core structure (FIG. 2C). The active enzyme reconstituted deoxyribozyme then binds to the reporter substrate (here it is fluorescent Substrate F), cleaves the reporter substrate thereby generating a detectable signal. Substrate F contains a fluorophore fluorescein (FAM) label and a quencher carboxytetramethylrhodamine (TAMRA). When Substrate F is cleaved by the activated deoxyribozyme, the FAM and TAMRA are separated, thereby permitting fluoescein to give a detectable fluorescent signal.

We next conducted experiments that determined the level of fluorescence in a solution of fluorescent substrate F and biE6-10 incubated in the absence (line 2) or presence (line 3) of A20 DNA (20 nucleotides in length) analyte at pH 7.4 and room temperature. Fluorescent intensities at 517 nm are represented as functions of the incubation time. Line 1 shows substrate alone. The results show that without DNA analyte A20, the fluorescence F of the solution is stable at the concentration of biE6-10h used (100 nM). Addition of DNA analyte triggered a 10-fold increase in fluorescence measured at (517 nm) during 1 hour of incubation (line 2). A notable drop in fluorescence was observed after the $3^{rd}$, $4^{th}$ $5^{th}$ and $6^{th}$ measurements, which can be explained by photo-bleaching of the fluorescein dye due to frequent irradiation. These results show that in the absence of DNA or RNA analyte, the binary deoxyribozyme is inactive due to dissociation of its two parts, and that addition of analyte (A20) DNA complementary to the analyte binding arms triggered reformation of the deoxyribozyme catalytic core thereby restoring its ability to cleave the phosphodiester bond in the substrate causing fluorescence. An increase in the fluorescence level in the solution after adding A20 complementary to the analyte binding arms was obvious and distinct even after only 10 minute incubation. The binary deoxyribozyme biE6-10 was about 5 times slower than the parent E6 enzyme (data not shown). This is probably due to reduced stability of the enzyme-substrate catalytic complex.

Similar results were obtained for biE6-10h, however, a longer incubation time was required to achieve a 5-fold increase in fluorescence due to reduced stability of the tertiary complex. This is because the two intra-strand stem-loops in biE6-10h stabilize the dissociated state compared to the probe biE6-10 that does not have stem loops. However, although the biE6-10h probe was less efficient catalytically, it was more sensitive to SNPs that the biE6-10 probe, as is shown in Table 1. Persons of skill in the art will design their binary probes accordingly.

Figure 4:
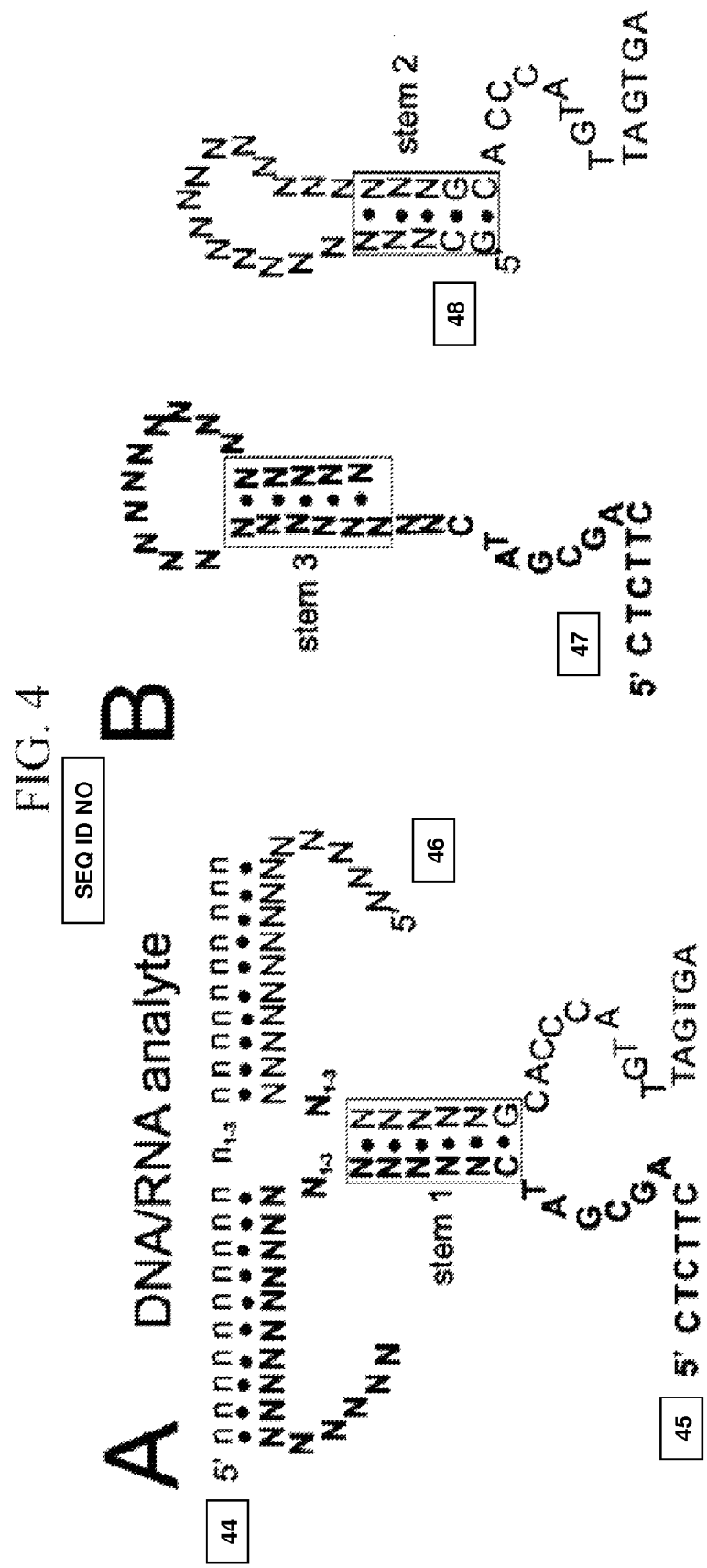
FIG. 4. A. Binary deoxyribozyme probe with structure stabilization arms; stem 1 forms when complementary probe binding arms hybridize; B. various stem-loop structures.

In a preferred embodiment the probe additionally has a structure stabilization arms (structure stabilization arm FIG. 1 call out no. 110) on the end of each strand, that form an internal stem-loop structure when the two halves (strands) of the probe are dissociated. It was shown earlier that introduction of a stem-loop structure to a DNA probe improves specificity of the probe-DNA analyte recognition (13 incorporated herein by reference). The stem-loop structures can be located at different positions where they prevent the dissociated binary probe from hybridizing to itself in the absence of analyte. FIG. 4 shows how in the absence of a DNA or RNA analyte, the probe binding arms hybridize forming stem 1. structure stabilization arm nucleotides on each antiparallel strand form a stem (named stem 2 and stem 3) can form a stem by hybridizing with a complementary sequence at other regions of the probe, for example with the probe binding arm to form stem 2 that also forms a loop structure, or with part of the probe binding arm and part of the analyte binding arm forming stem 3 and a loop. (FIG. 4B). Upon hybridization to the DNA analyte, the stems decompile and open, and the probe binding arm on each antiparallel strand hybridize thus reconstituting the catalytic core. (FIG. 4B).

We discovered that elongating the probe binding arm in biE6-10 that forms stem 1 to a length of 7-9 nucleotides led to detectable enzymatic activity even in the absence of DNA analyte, while shortening stem 1 to 4 base pairs substantially reduced the catalytic activity even in the presence of A20. Thus, 5-6 base-pairs are the preferred length for the probe binding arms for the biE6-10 and biE6-10h probes. However, routine experimentation will show the optimum length of all of the regions of the many different binary probes that can be made according to the present invention depending on their intended use. The probe binding arm is typically longer in probes designed to form stem and loop structures. If a probe is designed to have structure stabilization arm that hybridize with the probe binding arm, then the probe binding arm is protected (i.e. does not hybridize with the corresponding binding arm in the absence of analyte) and it can be longer. Typically structure stabilization arm are less than 15 nucleotides long, but this can vary.

The length and sequence of the deoxyribonucleotide linkers between the probe binding arm and analyte binding arms can also vary. When made of nucleotides, the length and the structure of the linkers can be varied preferably from N=1 to N=3. The linkers can also be non-nucleotide in nature such as a hexa-ethyleneglycol backbone provided by Integrated DNA Technologies (Coralville, Iowa, USA), although this would substantially increase the cost of the probe. Due to steric considerations pyrimidines are favored over purines when used as linker bases. Therefore in certain embodiments-linkers such as T, TT, TTT, C, CC, CCC are preferred. Nucleotide linker bases can be part of the analyte and/or probe binding arms, or they can be additional nucleotides added between the analyte and probe binding arms. Routine experimentation will determine the optimum probe design providing the highest rate of Substrate F cleavage in the presence of a DNA or RNA analyte with the lowest background in its absence.

To optimize the fluorescent read-out. of an assay, the cleavage of Substrate F can be monitored using FRET (fluorescence resonance energy transfer) and the concentrations of each component of the mixture can be optimized to achieve a fast and rigorous fluorescent response only after addition of DNA analyte. The same principles described above can be applied to optimize a cascade for binary ribozyme probes, which is described below. Previous reports describing other methods of nucleic acid analysis showed good discrimination parameters for the recognition of single mismatches positioned in the middle part of 15-mer oligonucleotides, however, elevated, non-physiologic temperatures of about 50 to about 70 degrees C. were required. Moreover, when a mismatch occurred at a terminal position of a 15-mer oligonucleotide, neither molecular beacons nor linear probes could reliably discriminate such substitutions, even at high temperatures or using special washing conditions. In order to examine the selectively of the biE6-10 deoxyribozyme probe, it was incubated with various oligonucleotides differing from the true A20 analyte target by only one base at various positions. The data shown in Table 1 demonstrate that both the biE6-10 and -10h probes recognized single nucleotide substitutions at any position of A20 DNA analyte, even at room temperature. It is particularly significant that the probes had good discrimination even (DF=13.0) of the terminally located mismatch at position 1 (A20-1). Methods of determining discrimination factors are set forth in the Examples.

Deoxyribozyme biE6-10h (that has structure stabilization arms) was able to reliably distinguish 19 mutants out of 20, while biE6-10 recognized only 17 mutants (Table 1). The Discrimination Factors in the case of biE6-10h were higher than those of biE6-10 for almost every single-base substituted oligonucleotide. These data speak in favor of the earlier suggestion that a combination of the binary approach with structural constraints in the probe design leads to improved selectivity.

TABLE 1

Discrimination factors for oligodeoxyribonucleotides differing from A20 by a single nucleotide*.

| SEQ ID | Oligodeoxyribonucleotides | | biE6-10h | biE6-10 |
|---|---|---|---|---|
| | Names | Sequences | DF | DF |
| 11 | A20 | ATGGAGAGAG TGGGTGCGAG | 1 | 1 |
| 12 | A20-1 | TTGGAGAGAG TGGGTGCGAG | 9.3 ± 4.3 | 6.4 ± 0.1 |
| 13 | A20-2 | AGGGAGAGAG TGGGTGCGAG | 1.4 ± 0.2 | 2.0 ± 0.4 |
| 14 | A20-3 | ATAGAGAGAG TGGGTGCGAG | 5.35 ± 0.8 | 1.8 ± 0.4 |
| 15 | A20-4 | ATGTAGAGAG TGGGTGCGAG | 44.6 ± 19.2 | 4.5 ± 0.8 |
| 16 | A20-5 | ATGGCGAGAG TGGGTGCGAG | 15.0 ± 7.4 | 3.3 ± 0.5 |
| 17 | A20-6 | ATGGATAGAG TGGGTGCGAG | 9.9 ± 2.7 | 1.8 ± 0.3 |
| 18 | A20-7 | ATGGAGGGAG TGGGTGCGAG | 3.6 ± 0.6 | 1.7 ± 0.1 |
| 19 | A20-8 | ATGGAGAAAG TGGGTGCGAG | 18.9 ± 8.6 | 3.2 ± 1.5 |
| 20 | A20-9 | ATGGAGAGCG TGGGTGCGAG | 1.6 ± 0.2 | 1.8 ± 0.1 |
| 21 | A20-10 | ATGGAGAGAT TGGGTGCGAG | 3.0 ± 0.4 | 1.4 ± 0.2 |
| 22 | A20-11 | ATGGAGAGAG GGGGTGCGAG | 1.7 ± 0.2 | 1.4 ± 0.3 |
| 23 | A20-12 | ATGGAGAGAG TAGGTGCGAG | 2.7 ± 0.6 | 1.2 ± 0.4 |
| 24 | A20-13 | ATGGAGAGAG TGTGTGCGAG | 2.5 ± 0.2 | 1.4 ± 0.2 |
| 25 | A20-14 | ATGGAGAGAG TGGTTGCGAG | 6.6 ± 1.1 | 2.0 ± 0.2 |
| 26 | A20-15 | ATGGAGAGAG TGGGAGCGAG | 13.0 ± 3.9 | 1.2 ± 0.1 |
| 27 | A20-16 | ATGGAGAGAG TGGGTTCGAG | 3.0 ± 0.2 | 2.8 ± 1.2 |
| 28 | A20-17 | ATGGAGAGAG TGGGTGTGAG | 9.3 ± 1.3 | 1.7 ± 0.5 |
| 29 | A20-18 | ATGGAGAGAG TGGGTGCCAG | 5.9 ± 1.7 | 1.3 ± 0.3 |
| 30 | A20-19 | ATGGAGAGAG TGGGTGCGGG | 1.4 ± 0.3 | 1.1 ± 0.1 |
| 31 | A20-20 | ATGGAGAGAG TGGGTGCGAA | 0.9 ± 0.1 | 1.0 ± 0.3 |

*Discrimination factors were calculated as the ratios of the probe fluorescence intensities at 517 nM in the presence of A20 (true target) to the fluorescence intensities in the presence of each mismatched oligonucleotide after subtraction of the background fluorescence. The mismatched positions are underlined. The data are the average of four independent measurements.

Certain embodiments of the invention are directed to the general structure of the binary deoxyribozyme or ribozyme probe which those skilled in the art can readily design based on the functional description and examples provided herein. In the broadest embodiment, the binary probe is non-naturally occurring. The probe has a first and a second oligodeoxynucleotide (for deoxyribozyme probes) or oligoribonucleotide (for ribozyme probes) strand that are antiparallel to one another, wherein the first oligonucleotide strand comprises:

a. At its 5'-terminus a substrate binding arm that is complementary to and hybridizes to a substrate cleaved by the active probe, that is flanked by a catalytic core, b. a catalytic core that cleaves the substrate, and that is flanked by a first probe binding arm, c. a first probe binding arm (typically of from 5 to 15 nucleotides in length) that is complementary to and hybridizes to the corresponding second probe binding arm in the second oligonucleotide strand when both analyte binding arms on the probe are bound to analyte, and that is flanked by a linker sequence, d. a linker sequence typically of from 1-3 nucleotides that is flanked by an analyte binding arm, and e. an analyte binding arm (from about 7-10 nucleotides if high selectivity is desired, or longer if high sensitivity is desired) that is complementary to and hybridizes to a all or a portion of an analyte, and that is optionally flanked by a structure stabilization arm.

The second oligonucleotide antiparallel strand comprises the same components only in an antiparallel order or reverse order with the substrate binding arm at its 3'-terminus, and the optional structure stabilization arm at the 5' end. If the probe is a deoxyribozyme probe all of the nucleotides N are deoxyribonucleotides. If the probe is a ribozyme probe all of the nucleotides N are ribonucleotides.

Other embodiments are directed to variations of the binary probe structure that optimize analyte discrimination parameters. Additional changes that may increase the selectivity of the probe include shortening the analyte, for example from 20 to 14 nucleotides, or increasing the reaction temperature to 37° C., which is still within physiologic conditions that can eventually permit analyte analysis in live cells in culture or in vitro. Other embodiments include varying the length of the probe binding arm from about 8 to about 15 nucleotides, or varying the placement and length of the structure stabilization arm. In other embodiments the substrate binding arm on each strand of the binary probe can be varied to accommodate different substrates known in or designed by those skilled in the art. Since the oligonucleotide strands of the binary probe are simple nucleotide sequences they can be made to order by various existing companies such as Integrated DNA Technologies (Coralville, Iowa, USA).

Another way of varying the probe is by using DNA or RNA analytes containing recognition domains in adjacent positions that are separated by 1, 2 or 3 nucleotides within the analyte (as is shown in FIG. 4A). In this embodiment, the analyte binding arms bind to the respective recognition domains in the analyte, but there is a 1-3 nucleotide gap in the analyte between these domains that does not have a corresponding complementary sequence in the probe to bind to. This gap may increase stability of the tertiary complex and improve catalytic efficiency which can in turn improve the speed of the reaction or increase sensitivity. Such manipulations are within routine experimentation by those skilled in the art.

Certain embodiments of the invention are directed to truncated forms of the deoxyribozyme binary probe ("the truncated probe"). In its simplest form the truncated probe strand has only probe binding arms, and the catalytic core. Users can customize the other regions of the probe. In another embodiment the truncated probe strands have the substrate binding arms, the catalytic core, the probe binding arm and the linker sequence. Various truncated forms of the probes come within the scope of the invention. One embodiment of a kit for detecting DNA or RNA in a sample would have a truncated probe (substrate binding arms, catalytic core, probe binding arm and linker) and the appropriate substrate. The user can customize the probe with any desired analyte binding arm. Alternatively diagnostic kits would have one or more substrates, and one or more complete binary deoxyribozyme probes with predetermined analyte binding arms that bind to a specific analyte that indicates the presence (or absence) of a specific analyte (such as a virus, bacterial endotoxin, cancer antigen) indicating the presence of a condition such as a disease including cancer. In one embodiment, a multiplex format is prepared having different binary deoxyribozymes probes that recognize different substrates (for example fluorogenic substrates) for each different analyte. In an embodiment the fluorogenic substrates will be labeled by differently colored fluorophores, enabling assays to be carried out that simultaneously detect different targets in the same reaction. A large variety of reporter substrates including fluorophores can be used (such as FAM, TET, TAMRA and others known in the art, and quenchers (such as Dabcyl, TAMRA, Iowa Black™, Black Hole Quencher®-1, Black Hole Quencher®-2) are commercially available (IDT Inc.).

The present binary probes, especially the deoxyribozyme probes, are less expensive than MB. The new binary probe-based technology requires synthesis of only two analyte binding arms for each different probe. Standard desalting provides sufficient purity for the oligonucleotides of such lengths. All other components of the probe, such as the double labeled fluorescent substrate or oligonucleotide immobilized nanoparticles, are universal for all assays. If applied for analysis of many different single nucleotide polymorphisms (SNPs), out of several million existing in human genome, the new approach will offer a substantially lower price for each assay compared to MB or other conventional methods, plus increased accuracy and the ability to work at moderate physiologic conditions. The binary deoxyribozyme/ribozyme detection system for DNA and RNA can be applied in virus diagnostics and mRNA analysis without prior PCR amplification. Since DNA-RNA and DNA-DNA hybrids have different structural parameters, the binary deoxyribozyme constructions should be customized for RNA in order to obtain highly specific and sensitive recognition of RNA targets.

The binary probes of the present invention may be separated from any portion of the single-stranded nucleic acid substrate that remains attached to the enzymatic DNA molecule by site-specific hydrolysis at the appropriate cleavage site. Separation of the enzymatic DNA molecule from the substrate (or "cleavage product") allows the enzymatic DNA molecule be reused to carry out another cleavage reaction.

Amplification of the Catalytic Activity of the Binary Deoxyribozyme/Ribozyme Probe Amplification of the catalytic activity of the binary deoxyribozyme/ribozyme probe using a cascade of cross-catalytic cleaving deoxyribozymogens/ribozymogens and fluorescent detection of the cascade activity is desirable. In order to attain sensitivity close to that obtainable by PCR, the catalytic activity of the binary deoxyribozyme//ribozyme probe is optimized using cross-catalytic cleavage of deoxyribozymogens/ribozymogens to create a cascade that causes the exponential growth of catalytically active molecules of the deoxyribozymes/ribozymes in solution. The catalytically active molecules cleave the substrate such as a fluorescent substrate, which leads to the increase of the signal such as fluorescence of the sample. In one embodiment of the invention described in more detail below, the active binary deoxyribozyme or ribozyme probe (activated by binding to analyte) hybridizes to a complementary sequence on a first inactive cross-catalytic deoxyribozymogen or a ribozymogen (such as I1 where "I" means inactive), thereby activating it (forming A1 where "A" means active). The activated deoxyribozyme (A1 active) hybridizes to a second inactive cross-catalytic deoxyribozymogen or a ribozymogen (I2), thereby activating it (forming A2). Activated A2 then hybridizes to I1 and starts the cycle all over. The autocatalytic cascade is capable of an exponential amplification of catalysis that dramatically enhances the positive signal. The catalytic activity of the cascade can be detected using fluorescent resonance energy transfer or optically using gold nanoparticles. When the reaction has gone long enough the reporter substrate is added and the signal generated by the reporter substrate is measured. If there is a signal, then it can be concluded that the analyte was present in the sample and triggered the cascade.

The use of DNA catalysis as advanced biosensors is efficient because catalytic DNAs are chemically stable, easy to produce, biocompatible, and amenable to rational design (Peracchi, A. 2005 Chembiochem. 6:1316-1322). Deoxyribozyme-based biosensors for metal ions (Lu, Y.; et al. Biosens Bioelectron. 18:529-540); and ATP (Lu et al., Anal Chem. 76:1627-1632; Cho, E. J. et al., 2005. ATP. J Am Chem Soc. 127:2022-2023) have been developed recently (the references above are incorporated herein by reference. The steps below will work for binary ribozyme probes as well.

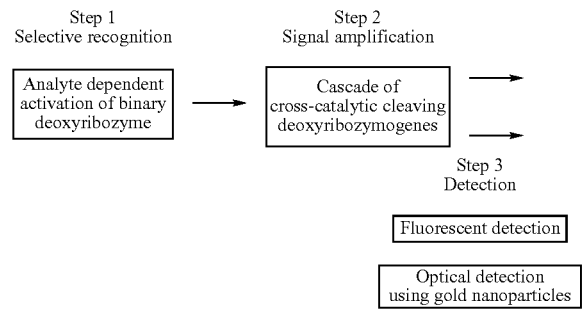

The deoxyribozyme based machinery for DNA/RNA recognition has three steps. At the first step the analyte is recognized by the binary deoxyribozyme and binds to complementary nucleotides in the deoxyribozyme analyte binding arms. Step 1 assures high recognition specificity and generates an active deoxyribozyme. In a preferred embodiment the active probe (activated by binding to analyte) triggers a cascade of cross-catalytic cleaving deoxyribozymogens or ribozymogens. This cascade amplifies the signal, for example a fluorescent signal. A deoxyribozymogen or ribozymogens cascade can be created for most ribozymes or deoxyribozymes using routine experimentation. Any cascade triggered by the activated probe can be used. Finally, the signal, which can be either fluorescent or optical, is read out.

Figure 6:
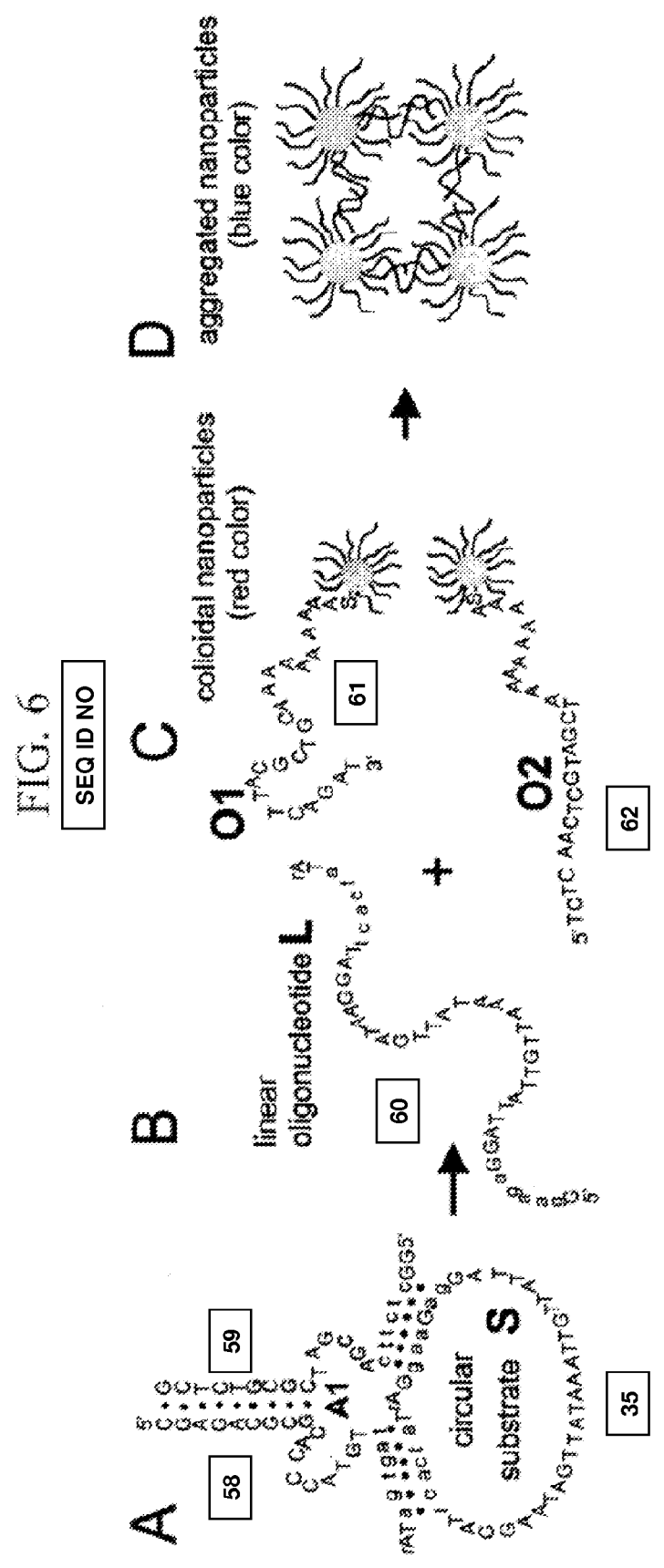

In one embodiment the signal is optical and uses gold nanoparticles. FIG. 6. Fluorescent detection of the deoxyribozyme enzymatic activity has been described and these methods can be readily adapted to the new technology. (Singh, K. K, et al., 1999 RNA. 5:1348-1356; Stojanovic, M. N, et al., Chembiochem. 2:411-415, incorporated herein by reference). Optical detection using gold nanoparticles for example, provides the simplest signal visualization. All three steps can be carried out simultaneously in one reaction mixture. The fluorescent or optical signal takes from several minutes to several hours to develop, dependent on the analyte concentration.

Levy and Ellington introduced a cascade that had two complementary deoxyribozymogens that were inactivated by circularization (Levy, M., Ellington, A. D. 2003 Proc Natl Acad Sci U S A. 100:6416-6421, incorporated herein by reference). In order to prove that the catalytic activity of the binary deoxyribozyme can be amplified using a cascade of cross-catalytic cleaving deoxyribozymogens, we designed and studied the nucleic acid constructions depicted in FIG. 5A using binary probes derived from E6 as a parent catalyst. These molecules (I1 and I2, A1 and A2, the substrate and the probe biE6-6II) can be used for any deoxyribozymes or ribozymes that can cleave the following substrate: NNN NNA TrAG GNN NNN (SEQ ID NO: 32), where Ns are deoxyribonucleotides or ribonucleotides. Certain embodiments of the invention are directed to the binary deoxyribozyme probes: biE6-10, biE6-10h, biE6-6II, I1, I2, A1, and A2.

Figure 5D:
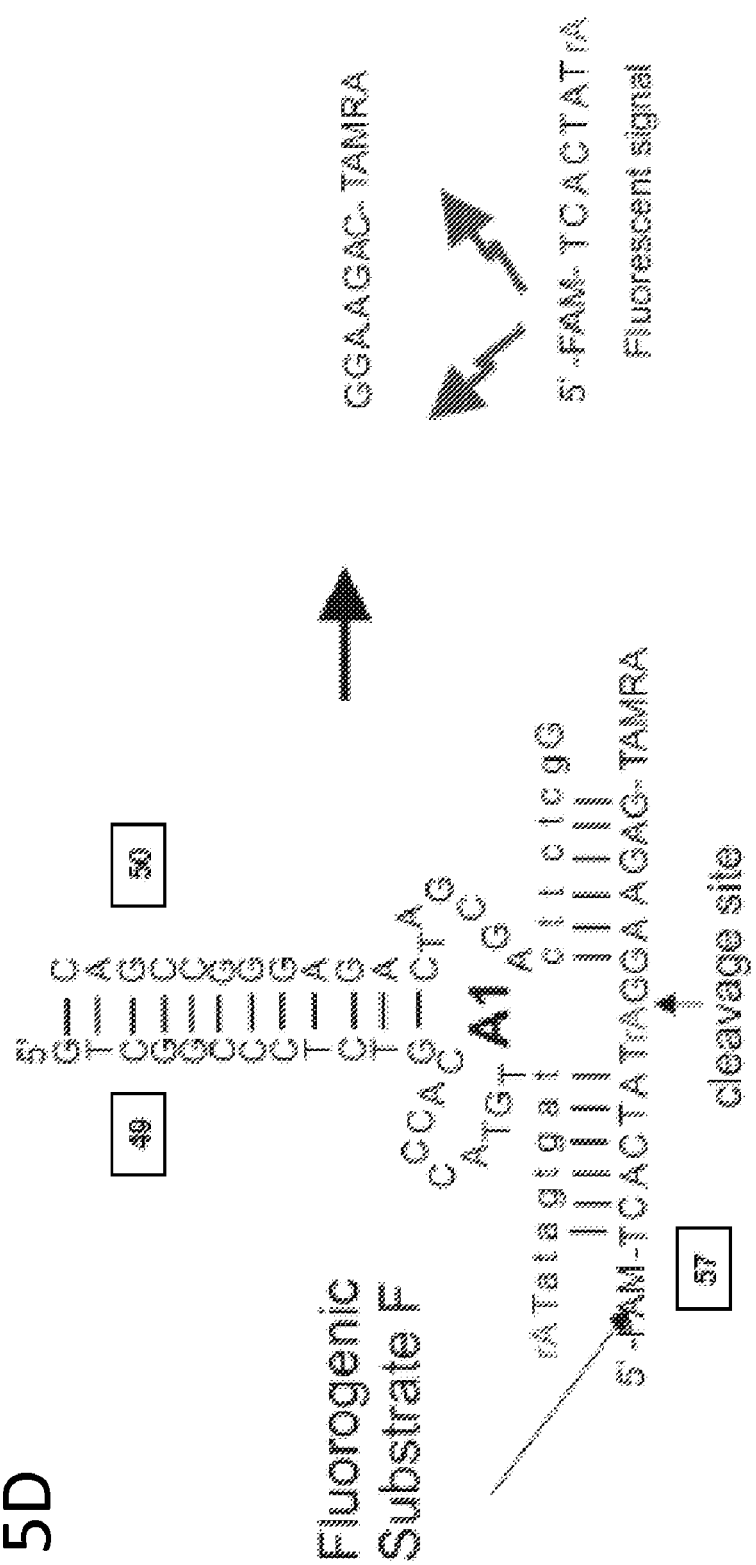
FIG. 5. Signal amplification by a cascade of cross-catalytic cleaving deoxyribozymogens. A: Structures of inactive and active forms of deoxyribozymogens; B: Binary deoxyribozyme biE6-6II recognizes A20 DNA analyte and cleaves I1; C: Cleavage of inactive I2 by active A1 produces active A2, which can, in turn, cleave inactive I1 to reproduce active A1. D: FRET-based detection of binary deoxyribozyme enzymatic activity. E: Fluorescence response of the cascade of deoxyribozymogens to the presence of different analyte concentrations after 3, 5, and 6 hours of incubation.

In our exemplary cascade, fluorogenic substrate F and deoxyribozymogens I1 and I2 along with binary deoxyribozyme biE6-6II were incubated in different concentrations of A20 DNA analyte. Upon hybridization of the two parts of biE6-6II to A20, catalytically active biE6-6II is formed in solution (FIG. 5B). This active enzyme is able to recognize and cleave catalytically inactive I1 generating the catalytically active deoxyribozyme A1. In order to initiate the cascade, the activated probe is not designed to cleave the substrate F. Instead the substrate binding arms on the binary probe are complementary to a nucleotide sequence in a deoxyribozymogen, such as I1, which is cleaved by the activated probe to start the cascade. When I1 is cleaved, it separates from the probe becoming activated to A1, which in turn, is able to recognize, hybridize with and cleave the inactive I2 deoxyribozymogen, thereby generating active A2. (FIG. 5C). A2, in turn, can hybridize with and cleave the inactive I1 deoxyribozymogen, thereby generating active A1. The process is repeated many times in solution thereby increasing exponentially the concentration of A1 and A2 over the duration of the incubation. A1 is able to cleave fluorogenic F substrate F (FIG. 5D), which allows convenient detection of deoxyribozyme activity.

Certain embodiments are directed to this cascade and others modeled on it in which the dissociated binary probe binds to analyte thereby being activated and initiating a cascade that amplifies the number of molecules that can bind to a reporter substrate such as substrate F.

Figure 5E:
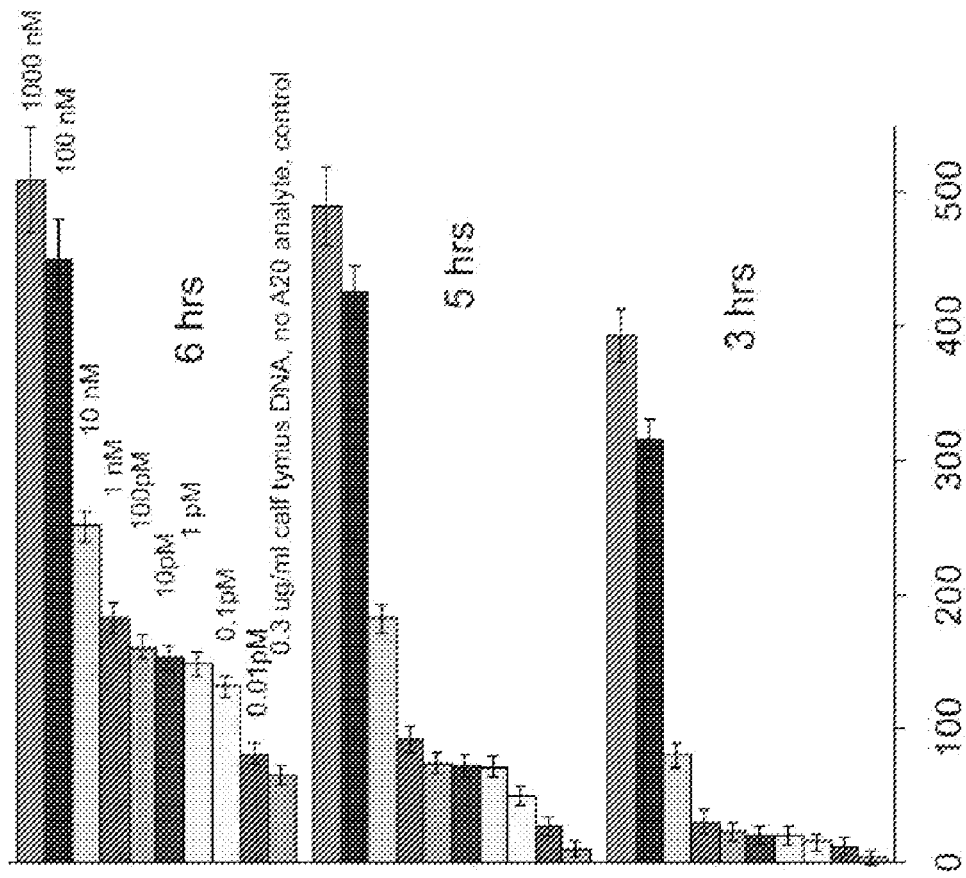

We found that after 3 hours of incubation, as little as 10 nM of A20 was reliably detected in solution. After 6 hours, 0.1 picoMoles A20 (One trillionth ($10^{-12}$) of a mole) gave fluorescence statistically higher than the background fluorescence (background was measured in the absence of A20 (FIG. 5E). This represents a high level of sensitivity for a fluorescence-based technique. In certain embodiments the assay is optimized by manipulating the concentration of the I1 and I2. It may also be possible to change the structure of the F substrate in order to obtain low background fluorescence.

Table 2 gives the SEQ ID NO. and sequence for various embodiments of the invention.

TABLE 2

```
SEQ ID NO. 1
Truncated probe with catalytic core and probe binding arm based on biE6-10, strand A:
5'-AGC GAT CAG TTC-3'

SEQ ID NO. 2
Truncated probe with catalytic core and probe binding arm based on biE6-10, strand B:
5'-GAA CTG CAC CCA TGT-3'

I1 = SEQ ID NO. 3 Cross-catalytic deoxyribozymogen
5'-GTC GGC CCT CTG CACCCATGTTAGTGATA TrAG GCTCTTCAGCGAT CAG
AGG GCC GAC-3'

I2 = SEQ ID NO. 4 Cross-catalytic deoxyribozymogen
5'-CACG CGGCTCTG CACCCATGTTATCACTA TrAG GAAGAGCAGCGAT
CAGAGCCG CGTG-3'
```

TABLE 2-continued

```
biE6-10h-Strand A SEQ ID NO. 5
5'-CTC TTC AGC GAT CAG TTC TT -3'

Truncated probe: Substrate binding arm, catalytic core, probe binding arm; and linkers;
without analyte binding arm, and structure stabilization arm.

biE6-10h-Strand B-SEQ ID NO 6
5'- TT GAA CTG CAC CCA TGT TAG TGA-3'

Truncated probe: Substrate binding arm, catalytic core, probe binding arm; and linkers;
without analyte binding arm, and structure stabilization arm.

biE6-10 Strand A- SEQ ID NO. 7
5'-CTC TTC AGC GAT CAG TTC-3'

Truncated probe: Substrate binding arm, catalytic core, probe binding arm; without
linkers, analyte binding arm, and structure stabilization arm.

biE6-10- Strand B-8
CTC GCA CCC ATT GAA CTG CAC CCA TGT TAG TGA

Truncated probe: Substrate binding arm, catalytic core, probe binding arm; without
linkers, analyte binding arm, and structure stabilization arm.

SEQ ID NO. 9
biE6-6II
Strand A
GAAGAGC AGC GAT CAG TTC TT

Probe without analyte binding arm

SEQ ID NO. 10
biE6-6II Strand B
TT GAA CTG CAC CCA TGT TATCACTA

Probe without analyte binding arm
```

Assays of RNA or DNA Analytes Using Binary Probes

The present invention also provides nucleic acid hybridization assays for detecting RNA or DNA analyte targets using the deoxyribozyme/ribozyme binary probes of the invention. One embodiment is directed to a binary deoxyribozyme (or ribozyme) probe hybridization assay to detect an RNA or DNA analyte having a known nucleotide sequence in a sample, having the steps of: a) providing a binary deoxyribozyme (or ribozyme) probe comprising a nucleotide sequence that is complementary to and hybridizes to all or part of the known nucleotide sequence in the analyte, thereby activating the probe, b) providing a substrate that hybridizes to and is cleaved by the probe, thereby producing one or more signal products that can be detected, c) creating a mixture comprising the sample, the binary probe and the substrate, d) maintaining the mixture of step b) for a sufficient period of time and under reaction conditions that allow the analyte to hybridize to the complementary nucleotide sequence in the probe, thereby activating the probe which causes cleavage of the substrate, and e) determining that the analyte is present in the sample if the one or more signal products are detected.

Another embodiment is directed to an enzyme cascade assay for detecting a DNA or RNA analyte in a sample comprising a known nucleotide sequence, as described above and in the summary of invention. The analyte can be either DNA or RNA. The complementary analyte binding arms are designed and customized according to the analyte being assayed based on a known analyte nucleotide sequence. The binary probe can find the target analyte region in DNA/RNA molecules of any size, because the probe will recognize and hybridize with the critical target analyte region nucleotides. When the DNA or RNA is longer than the analyte binding arm, the excess nucleotides (that do not hybridize with the probe) will overhang on each side. The probe will be able to detect low quantities of nucleic acid in a sample. Ideally one molecule of specific single stranded DNA or RNA will be detected by binary deoxyribozyme.

It has recently been noted that certain oligonucleotides are able to recognize and bind molecules other than oligonucleotides with complementary sequences. These oligonucleotides are often given the name "aptamers". For example, Ellington et al describe RNA molecules that are able to bind a variety of organic dyes (Nature, 346:818 822, 1990), while Bock et al describe ssDNA molecules that bind human thrombin (Nature, 355:564 566, 1992). Similarly, Jellinek et al describe RNA ligands to basic fibroblast growth factor (Proc. Natl. Acad. Sci. USA, 90:11227 11231, 1993). Thus, it is further contemplated herein that the binary probes of the present invention may be engineered according to the within-described methods to display a variety of capabilities typically associated with aptamers.

Optical Detection of Deoxyribozyme/Ribozyme Catalytic Activity with Nanotechnology Fluorescent detection is the easiest way to monitor deoxyribozyme/ribozyme activity. However, certain embodiments include using nanoparticle-based approaches that permit visual detection of specific nucleic acids are contemplated. Oligonucleotide modified gold nanoparticles have been suggested as a tool for nucleic acids analysis (reviewed in Rosi, N. L. et al., Chem Rev. 105:1547-1562, incorporated herein by reference). When 13-nm oligonucleotide immobilized gold particles were mixed with target DNA, the color of the solution changed from red to blue upon the analyte-directed aggregation of the particles. Further development of the nanoparticle-based techniques have recently led to the calorimetric scatter and the bio-bar-code amplification methods, which allow impressive 20,000 and 5-10 DNA copy sensitivity, respectively (Mirkin, C. A. et al. 1996 Nature. 382:607-609; Storhoff, J. J. et al. 2004 Nat. Biotechnol. 22:883-887; Nam, J. M, et al. 2004 J. Am. Chem. Soc. 126:5932-5933, incorporated herein by reference).

In one embodiment aggregation of gold nanoparticles is used as the optical signal. Activation of the binary probe by binding the analyte triggers the deoxyribozyme/ribozyme to cleave a circular substrate (Described below as Substrate S). The resulting linear product will trigger hybridization-promoted gold nanoparticle aggregation, which is accompanied by a change in the solution color from red to blue. Detection of a single DNA molecule with visualization of the signal by the naked eye using nanotechnology is possible.

Figure 7B:
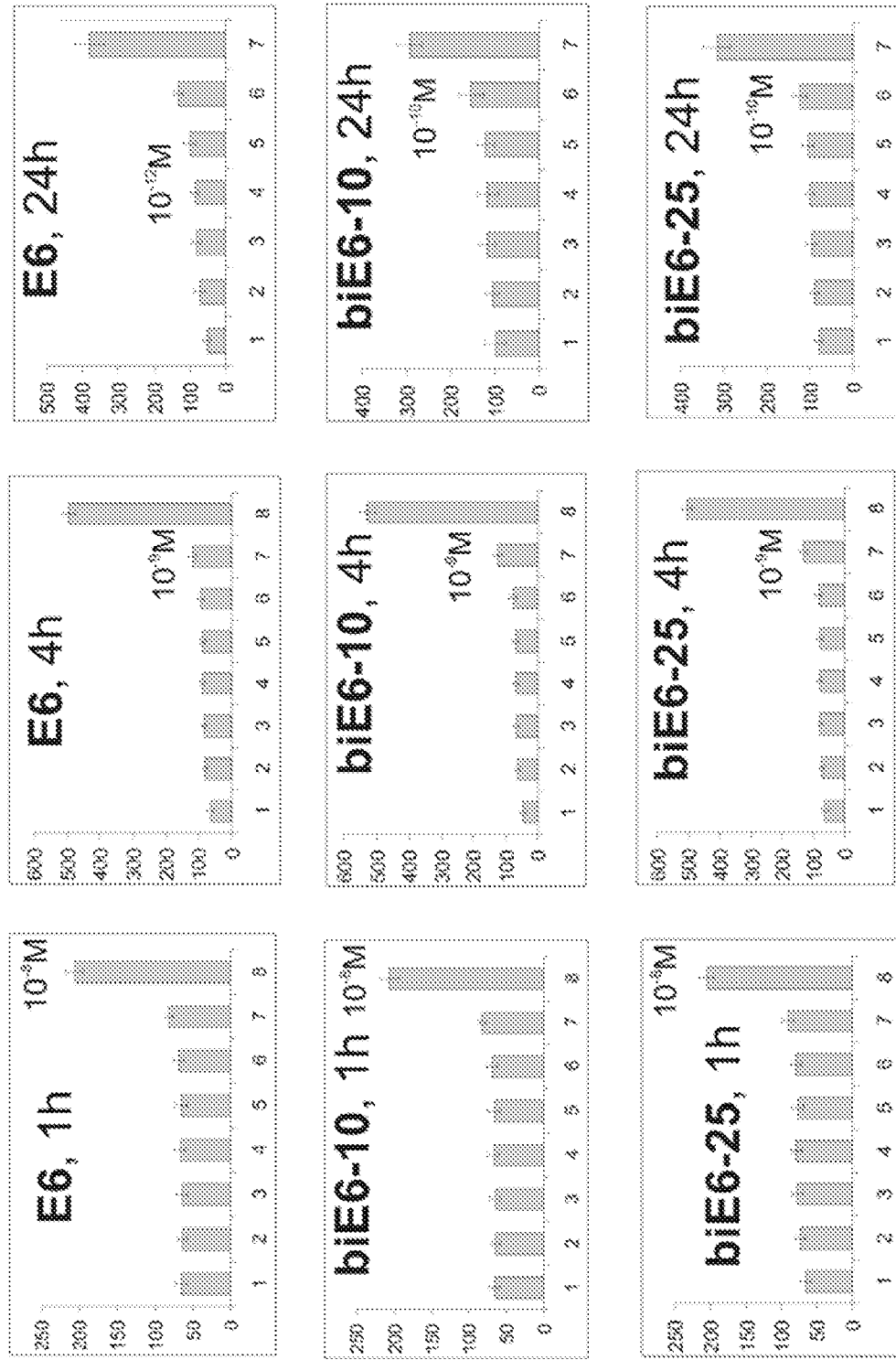
FIG. 7. Nucleotide analyte sensitivity of binary deoxyribozyme probe with elongated analyte binding arms. A: Structures of biE6-25 and A61 DNA analytes. B: Substrate F (1 µM) was incubated with different concentrations of E6 (upper row), or with 100 nM biE6-10 (middle row) and 100 nM biE6-25 (bottom row) and different concentrations of A20 or A61 DNA analytes, respectively. The fluorescent intensities at 517 nM were taken after 1, 4, and 24 hours of incubation. Bars 1: only F substrate; Bars 2: $10^{-14}$M E6 (only for upper row) or binary deoxyribozymes in the absence of cognate analytes (middle and bottom rows); Bars 3-8 fluoresce intensities in the presence of different concentration of E6 or analyte; Bars 3: $10^{-13}$ M; Bars 4: $10^{-12}$ M; Bars 5: $10^{-11}$M; Bars 6: $10^{-10}$M; Bars 7: $10^{-9}$ M; Bars 8: $10^{-8}$M. The data are average of three independent measurements. The E6 or analyte concentrations that were significantly higher than the background fluorescence are indicated in each panel.

The principle design of an Au nanoparticle-based detection system for deoxyribozyme/ribozyme activity is schematically shown in FIG. 7. A circular oligonucleotide Substrate S (FIG. 7A) and two types of oligonucleotide-immobilized nanoparticles (FIG. 7C) will be added to the reaction mixture containing binary deoxyribozyme and deoxyribozymogens. The two species of the nanoparticles differ by the oligonucleotides O1 and O2 immobilized on their surface. After the cascade of cross-catalytic cleaving deoxyribozymogens generates active deoxyribozymes, Substrate S is cleaved by deoxyribozyme A1 (FIG. 7A). The resulting oligonucleotide L (FIG. 7B) triggers aggregation of the nanoparticles by hybridizing to complementary oligonucleotides O1 and O2. (FIGS. 7C and D). The Nanoparticle aggregation leads to a change in the color of the solution from red to blue.

Attaching oligonucleotides O1 (5'TCT CAA CTC GTA GCT-A10-SH)(SEQ ID No: 33) and O2 (SH-A10-CGT CGC ATT CAG GAT-3')(SEQ ID NO: 34) to gold nanoparticles is accomplished as described previously (Mirkin, C. A., et al. 1996. Nature. 382:607-609). The structure of these two oligonucleotides permits them to hybridize to oligonucleotide L. To optimize the DNA analyte concentration the binary deoxyribozyme, I1, I2, oligonucleotide S and gold nanoparticles labeled with O1 and O2 are incubated in the presence of different concentrations of DNA analyte. The light absorption of the solution at 700 nM is monitored and the sensitivity limit of this system will is thus determined.

The circular substrate is not able to trigger DNA dependent gold nanoparticle aggregation. After linearization of substrate S the nano-particles will aggregate producing a signal that can be recognized optically. Circular substrate S can be synthesized from its liner precursor 5'-pATT GAT AAG GAT TCA CTA TrAG GAA AGA GGA TTA TTG TTA AAT (SEQ ID NO: 35) by means of ligation reaction mediated by T4 DNA ligase in the presence of complementary oligonucleotide 5'-CTT ATC AAT ATT TAA CAA (SEQ ID NO: 36). In order to remove all traces of linear DNA contaminants the final product is treated with exonuclease and purified by PAGE. The circularization reaction will be carried out with T4 DNA ligase (Promega) and a splint oligonucleotide CTT ATC AAT ATT TAA CAA (SEQ ID NO: 37). The concentration of linear substrate will be 100 nM, and the splint oligonucleotide will be 120 nM. The reaction will be allowed to proceed for 16 hours at room temperature and the circular product will be isolated on denaturing (7 M urea) 20% polyacrylamide gels. After gel purification S will be treated with exonuclease (Promega) to remove any remaining linear nucleic acids.

The resulting circular Substrate S can be examined for its ability to serve as a substrate for deoxyribozymes, including those used in the cascade such as A1. Substrate S will be incubated with the binary probe including A1 or a mixture including the binary deoxyribozyme, I1, I2 and S in the presence or absence of DNA analyte. The cleavage rate of S will be determined after PAGE separation of the reaction mixture.

The present invention contemplates using any substrate that can be cleaved by the binary probe and any means of detection of the cleaved product known to those skilled in the art and adaptable with routine experimentation.

EXAMPLES

Materials

DNAse/RNAse free water was purchased from Fisher Scientific Inc. (Pittsburgh, Pa.) and used for buffers, and for stock solutions of oligonucleotides. Oligonucleotides were custom-made by Integrated DNA Technologies, Inc. (Coralville, Iowa) or by TriLink BioTechnologies, Inc (San Diego, Calif.). Fluorescent spectra were taken on a Perkin-Elmer (San Jose, Calif.) LS-55 Luminescence Spectrometer with a Hamamatsu Xenon lamp. Experiments were performed at the excitation wavelength of 485 nm and emission scan of 500-550 nm. The emitting intensities at 517 nm were taken for the calculation of the discrimination factors. The data of four independent experiments will be processed using Microsoft Excel.

Binary Deoxyribozyme Assay

The solutions of F substrate (200 nM), biE6-10 (100 nM each strand) or biE6-10h (200 nM each of the strand) were mixed in 50 mM $MgCl_2$, 50 mM HEPES, pH 7.4 and split in 4 tubes 120 uL in each. A20 was added to the final concentration of 80 nM. Control samples did not contain analyte of it's analogues. The fluorescent emission spectrum was recorded after indicated incubation time. The fluorescence intensities at 517 nM were taken for the calculation of the DFs.

Discrimination Factors (DFs) for biE6 Constructions

The solutions of F substrate (200 nM), biE6-10 (100 nM each strand) or biE6-10h (200 nM each of the strand) were mixed in 50 mM $MgCl_2$, 50 mM HEPES, pH 7.4 and split in 24 tubes 120 uL in each. A20 or one of the single base-substituted oligodeoxynucleotide (for structures see Table 1) were added to the final concentration of 80 nM. Control samples for measurement of the background fluorescence did not contain analyte or analyte analogues. After 2 hours incubation room temperature the fluorescent emission spectrum were measured. The fluorescence intensities at 517 nM were taken for the calculation of the DFs. The average values represent the results of four independent experiments.

In the foregoing specification, the invention has been described with reference to specific embodiments. It will, however, be evident that various modifications and changes may be made thereto without departing from the broader spirit and scope of the invention. The specification and drawings are, accordingly, to be regarded in an illustrative rather than a restrictive sense.

What is claimed is:

1. A non-naturally occurring binary oligonucleotide enzyme probe comprising:
   i) a first oligonucleotide strand comprising:
      a. at its 5'-terminus a first substrate binding arm that is complementary to and hybridizes to a first portion of a substrate,
      b. a first catalytic core fragment that flanks the first substrate binding arm,
      c. a first probe binding arm that flanks the first catalytic core fragment, which first probe binding arm is complementary to and hybridizes to second probe binding arm on a second oligonucleotide strand when the first and second oligonucleotide strands are bound to the analyte,
      d. at its 3'-terminus a first analyte binding arm that flanks the first probe binding arm, which first analyte binding arm is complementary to and hybridizes to a first portion of the analyte; and
      e. a first structure stabilization arm at the 3' terminus flanking the first analyte binding arm, which first structure stabilization arm is complementary to and hybridizes to a nucleotide sequence in the first oligonucleotide strand, and
   ii) the second oligonucleotide strand comprising:
      a. at its 3'-terminus a second substrate binding arm that is complementary to and hybridizes to a second portion of the substrate,
      b. a second catalytic core fragment that flanks the second substrate binding arm,
      c. the second probe binding arm that flanks the second catalytic core fragment, which second probe binding arm is complementary to and hybridizes to the first probe binding arm when the first and second oligonucleotide strands are bound to the analyte,
      d. at its 5'-terminus a second analyte binding arm that flanks the second probe binding arm, which second analyte binding arm is complementary to and hybridizes to a second portion of the analyte, and
      e. a second structure stabilization arm at the 3' terminus flanking the second analyte binding arm, which second structure stabilization arm is complementary to and hybridizes to a nucleotide sequence in the second oligonucleotide strand, and
      wherein upon binding of the probe to the analyte, the first and second catalytic core fragments form a single active catalytic core that cleaves the substrate, thereby generating a detectable signal.

2. The non-naturally occurring binary oligonucleotide enzyme probe of claim 1, wherein the first structure stabilization arm hybridizes to a nucleotide sequence in the first analyte binding arm, and the second structure stabilization arm hybridizes to a nucleotide sequence in the second analyte binding arm.

3. The binary oligonucleotide enzyme probe of claim 1, wherein the analyte binding arms are from about 7 to about 50 nucleotides long.

4. The binary oligonucleotide enzyme probe of claim 1, wherein the analyte binding arms bind to the probe binding arms on the respective first and second strands through a linker.

5. The binary oligonucleotide enzyme probe of claim 4, wherein the linker comprises two nucleotides on the ends of the analyte binding arms and the probe binding arms on the respective first and second strands through which the two arms are bound, or the linker comprises a molecule added between the analyte and the probe binding arms on the respective first and second strands through which the two arms are bound.

6. The binary oligonucleotide enzyme probe of claim 2, wherein the structure stabilization arms are from about 4 to about 10 nucleotides long.

7. The binary oligonucleotide enzyme probe of claim 1, wherein the first oligonucleotide strand comprises a base sequence of SEQ ID NO. 1, and the second oligonucleotide strand comprises a base sequence of SEQ ID NO. 2.

8. The binary oligonucleotide enzyme probe of claim 1, wherein the first oligonucleotide strand comprises a base sequence of SEQ ID NO. 5, and the second oligonucleotide strand comprises a base sequence of SEQ ID NO. 6.

9. The binary oligonucleotide enzyme probe of claim 1, wherein the probe is a ribozyme probe.

10. The binary oligonucleotide enzyme probe of claim 1, wherein the probe is a deoxyribozyme probe.

11. The binary oligonucleotide enzyme probe of claim 1, wherein the first structure stabilization arm at the 3' end on the first strand hybridizes to at least a portion of the first probe binding arm to form a stem and loop, and the second structure stabilization arm at the 5' end on the second strand hybridizes to at least a portion of the second probe binding arm to form a stem and loop.

12. The binary oligonucleotide enzyme probe of claim 1, wherein the first structure stabilization arm at the 3' end on the first strand hybridizes to at least a portion of the first analyte binding arm to form a stem and loop, and the second structure stabilization arm at the 5' end on the second strand hybridizes to at least a portion of the second analyte binding arm to form a stem and loop.

13. A hybridization assay to detect a nucleic acid analyte having a known nucleotide sequence in a sample, comprising the steps of:
 a) providing the non-naturally occurring binary oligonucleotide enzyme probe of claim 1,
 b) providing a substrate that hybridizes to and is cleaved by the probe in the presence of the analyte, thereby producing a detectable signal,
 c) creating a mixture comprising the sample, the binary probe and the substrate,
 d) maintaining the mixture of step c) for a sufficient period of time and under reaction conditions that allow the analyte to hybridize to the analyte-binding arms of the probe, thereby activating the probe, which activated probe causes cleavage of the substrate, and
 e) determining whether the analyte is present in the sample based on the presence and/or magnitude of the detectable signal.

14. The assay of claim 13, wherein the detectable signal is fluorescent.

15. The assay of claim 13, wherein cleavage of the substrate results in a signal product that binds to and triggers aggregation of gold labeled nanoparticles.

16. The assay of claim 13, wherein the substrate comprises a fluorophore at one terminus and a quencher for the fluorophore at the other terminus.

17. The assay of claim 13, wherein the probe is a deoxyribozyme probe or a ribozyme probe.

18. A kit for a detecting a nucleic acid analyte comprising a known nucleotide sequence, comprising:
 i) a non-naturally occurring binary deoxyribozyme probe comprising an analyte binding arm that is complementary to and hybridizes to all or part of the known nucleotide sequence in the analyte, and further comprising a substrate binding arm that binds to and cleaves a first inactive cross-catalytic deoxyribozymogen, thereby forming a first active deoxyribozyme;
 ii) the first inactive cross-catalytic deoxyribozymogen that hybridizes to the substrate binding arm on the probe and is thereby cleaved to generate the first activated deoxyribozyme that is capable of hybridizing with both a substrate and a second inactive cross-catalytic deoxyribozymogen, and
 iii) the second inactive cross-catalytic deoxyribozymogen that hybridizes to the first active deoxyribozyme and is thereby cleaved to generate the second active deoxyribozyme that, in turn, hybridizes to and cleaves the first inactive cross-catalytic deoxyribozymogen, thereby generating the first active deoxyribozyme.

19. A kit for a detecting a nucleic acid analyte comprising a known nucleotide sequence, comprising:
 i) a non-naturally occurring binary ribozyme probe comprising an analyte binding arm that is complementary to and hybridizes to all or part of the known nucleotide sequence in the analyte, and further comprising a substrate binding arm that binds to and cleaves a first inactive cross-catalytic ribozymogen, thereby forming a first active ribozyme;
 ii) the first inactive cross-catalytic ribozymogen, that hybridizes to the substrate binding arm on the probe and is thereby cleaved to generate a first active ribozyme that is capable of hybridizing with both a substrate and a second inactive cross-catalytic ribozymogen, and
 iii) the second inactive cross-catalytic ribozymogen that hybridizes to the first active ribozyme and is thereby cleaved to generate a second active ribozyme that, in turn, hybridizes to and cleaves the first inactive cross-catalytic ribozymogen, thereby generating the first active ribozyme.

20. The kit of claim 18, further comprising a substrate that binds to and is cleaved by the first activated deoxyribozyme, thereby generating a detectable signal.

21. An enzyme assay for detecting a nucleic acid analyte comprising a known nucleotide sequence in a sample, the assay comprising the steps of:
 a) forming a mixture comprising:
 i. a non-naturally occurring binary deoxyribozyme probe comprising an analyte binding arm that is complementary to and hybridizes to all or part of the known nucleotide sequence in the analyte, and further comprising a substrate binding arm that binds to and cleaves a first inactive cross-catalytic deoxyribozymogen, thereby forming a first active deoxyribozyme;
 ii. the first inactive cross-catalytic deoxyribozymogen that hybridizes to the substrate binding arm on the probe and is thereby cleaved to generate a first active deoxyribozyme that is capable of hybridizing with both a substrate and a second inactive cross-catalytic deoxyribozymogen,
 iii. the second inactive cross-catalytic deoxyribozymogen that hybridizes to the first active deoxyribozyme and is thereby cleaved to generate a second active deoxyribozyme that, in turn, hybridizes to and cleaves the first inactive cross-catalytic deoxyribozymogen, thereby generating the first active deoxyribozyme, and iv. a substrate that hybridizes to and is cleaved by the first active deoxyribozyme to generate a detectable signal;
b) contacting the mixture with a sample containing the analyte and incubating the mixture under conditions that permit nucleic acid hybridization,
c) determining if analyte is present in the sample based on the presence and/or magnitude of the detectable signal.

22. An enzyme assay for detecting a nucleic acid analyte comprising a known nucleotide sequence in a sample, the assay comprising the steps of:
a) forming a mixture comprising:
i. a non-naturally occurring binary ribozyme probe comprising an analyte binding arm that is complementary to and hybridizes to all or part of the known nucleotide sequence in the analyte, and further comprising a substrate binding arm that binds to and cleaves a first inactive cross-catalytic ribozymogen, thereby forming a first active ribozyme;
ii. a first inactive cross-catalytic ribozymogen, that hybridizes to the substrate binding arm on the probe and is thereby cleaved to generate the first active ribozyme that is capable of hybridizing with both a substrate and a second inactive cross-catalytic ribozymogen,
iii. the second inactive cross-catalytic ribozymogen that hybridizes to the first active ribozyme and is thereby cleaved to generate a second active ribozyme that, in turn, hybridizes to and cleaves the first inactive cross-catalytic ribozymogen, thereby generating the first active ribozyme, and
iv. a substrate that hybridizes to and is cleaved by the first active ribozyme to generate a detectable signal;
b) contacting the mixture with a sample containing the analyte and incubating the mixture under conditions that permit nucleic acid hybridization,
c) determining if the analyte is present in the sample based on the presence and/or magnitude of the detectable signal.

23. A non-naturally occurring binary deoxyribozyme probe comprising two oligonucleotide strands, wherein the first oligonucleotide strand comprises a base sequence of SEQ ID NO. 7, and the second oligonucleotide strand comprises a base sequence of SEQ ID NO. 8.

24. A deoxyribozymogen identified by SEQ ID NO. 3.

25. A deoxyribozymogen identified by SEQ ID NO. 4.

26. A deoxyribozyme probe identified herein as biE6-6II comprising:
a) a first oligonucleotide strand A identified by SEQ ID NO. 9, and
b) a second oligonucleotide strand B identified by SEQ ID NO. 10.

27. A non-naturally occurring binary deoxyribozyme probe comprising two oligonucleotide strands, wherein the first oligonucleotide strand comprises a base sequence of SEQ ID NO. 9, and the second oligonucleotide strand comprises a base sequence of SEQ ID NO. 10.

28. The kit of claim 19, further comprising a substrate that binds to and is cleaved by the first activated deoxyribozyme, thereby generating a detectable signal.

29. The non-naturally occurring binary oligonucleotide enzyme probe of claim 4, wherein the molecule added between the analyte binding arms and the probe binding arms on the respective first and second strands through which the two arms are bound comprises from one to 3 nucleotides, or comprises a non-nucleotide linker.

30. The binary oligonucleotide enzyme probe of claim 29, wherein the non-nucleotide linker comprises an oligoethylene glycol molecule.

31. A kit for detecting a nucleic acid analyte comprising a known nucleotide sequence in a sample, comprising
a) a non-naturally occurring binary oligonucleotide enzyme probe comprising antiparallel oligonucleotide strands, wherein
i) the a first oligonucleotide strand comprises-comprising:
a. at its 5'-terminus a first substrate binding arm that is complementary to and hybridizes to a first portion of a substrate,
b. a first catalytic core fragment that flanks the first substrate binding arm,
c. a first probe binding arm that flanks the first catalytic core fragment, which first probe binding arm is complementary to and hybridizes to second probe binding arm on a second oligonucleotide strand when the first and second oligonucleotide strands are bound to the analyte, and
d. at its 3'-terminus a first analyte binding arm that flanks the first probe binding arm, which first analyte binding arm is complementary to and hybridizes to a first portion of the analyte; and
ii) the second oligonucleotide strand comprising:
a. at its 3'-terminus a second substrate binding arm that is complementary to and hybridizes to a second portion of the substrate,
b. a second catalytic core fragment that flanks the second substrate binding arm,
c. the second probe binding arm that flanks the second catalytic core fragment, which second probe binding arm is complementary to and hybridizes to the first probe binding arm when the first and second oligonucleotide strands are bound to the analyte, and
d. at its 5'-terminus a second analyte binding arm that flanks the second probe binding arm, which second analyte binding arm is complementary to and hybridizes to a second portion of the analyte, and
wherein upon binding of the probe to the analyte, the first and second catalytic core fragments form a single active catalytic core that cleaves the substrate is cleaved by the probe in the presence of the analyte, thereby generating a detectable signal, and
b) the substrate, which is cleaved by the probe in the presence of the analyte, thereby generating a detectable signal.

32. The binary oligonucleotide enzyme probe of claim 31, wherein the analyte binding arms are from about 7 to about 10 nucleotides long.

* * * * *

SEQUENCE LISTING

<160> NUMBER OF SEQ ID NOS: 65

<210> SEQ ID NO 1
<211> LENGTH: 12
<212> TYPE: DNA
<213> ORGANISM: Artificial Sequence
<220> FEATURE:
<223> OTHER INFORMATION: Synthetic Construct

<400> SEQUENCE: 1
agcgatcagt tc                                               12

<210> SEQ ID NO 2
<211> LENGTH: 15
<212> TYPE: DNA
<213> ORGANISM: Artificial Sequence
<220> FEATURE:
<223> OTHER INFORMATION: Synthetic Construct

<400> SEQUENCE: 2
gaactgcacc catgt                                            15

<210> SEQ ID NO 3
<211> LENGTH: 57
<212> TYPE: DNA
<213> ORGANISM: Artificial Sequence
<220> FEATURE:
<223> OTHER INFORMATION: Synthetic Construct

<400> SEQUENCE: 3
gtcggccctc tgcacccatg ttagtgatat aggctcttca gcgatcagag ggccgac    57

<210> SEQ ID NO 4
<211> LENGTH: 57
<212> TYPE: DNA
<213> ORGANISM: Artificial Sequence
<220> FEATURE:
<223> OTHER INFORMATION: Synthetic sequence

<400> SEQUENCE: 4
cacgcggctc tgcacccatg ttatcactat aggaagagca gcgatcagag ccgcgtg    57

<210> SEQ ID NO 5
<211> LENGTH: 20
<212> TYPE: DNA
<213> ORGANISM: Artificial Sequence
<220> FEATURE:
<223> OTHER INFORMATION: Synthetic sequence

<400> SEQUENCE: 5
ctcttcagcg atcagttctt                                       20

<210> SEQ ID NO 6
<211> LENGTH: 23
<212> TYPE: DNA
<213> ORGANISM: Artificial Sequence
<220> FEATURE:
<223> OTHER INFORMATION: Synthetic sequence

<400> SEQUENCE: 6
ttgaactgca cccatgttag tga                                   23

<210> SEQ ID NO 7
<211> LENGTH: 18
<212> TYPE: DNA

```
<213> ORGANISM: Artificial Sequence
<220> FEATURE:
<223> OTHER INFORMATION: Synthetic sequence

<400> SEQUENCE: 7
ctcttcagcg atcagttc                                              18

<210> SEQ ID NO 8
<211> LENGTH: 21
<212> TYPE: DNA
<213> ORGANISM: Artificial Sequence
<220> FEATURE:
<223> OTHER INFORMATION: Synthetic sequence

<400> SEQUENCE: 8
gaactgcacc catgttagtg a                                          21

<210> SEQ ID NO 9
<211> LENGTH: 21
<212> TYPE: DNA
<213> ORGANISM: Artificial Sequence
<220> FEATURE:
<223> OTHER INFORMATION: Synthetic sequence

<400> SEQUENCE: 9
gaagagcagc gatcagttct t                                          21

<210> SEQ ID NO 10
<211> LENGTH: 25
<212> TYPE: DNA
<213> ORGANISM: Artificial Sequence
<220> FEATURE:
<223> OTHER INFORMATION: Synthetic sequence

<400> SEQUENCE: 10
ttgaactgca cccatgttat cacta                                      25

<210> SEQ ID NO 11
<211> LENGTH: 20
<212> TYPE: DNA
<213> ORGANISM: Artificial Sequence
<220> FEATURE:
<223> OTHER INFORMATION: Synthetic construct

<400> SEQUENCE: 11
atggagagag tgggtgcgag                                            20

<210> SEQ ID NO 12
<211> LENGTH: 20
<212> TYPE: DNA
<213> ORGANISM: Artificial Sequence
<220> FEATURE:
<223> OTHER INFORMATION: Synthetic construct

<400> SEQUENCE: 12
ttggagagag tgggtgcgag                                            20

<210> SEQ ID NO 13
<211> LENGTH: 20
<212> TYPE: DNA
<213> ORGANISM: Artificial Sequence
<220> FEATURE:
<223> OTHER INFORMATION: Synthetic construct

<400> SEQUENCE: 13
agggagagag tgggtgcgag                                            20
```

```
<210> SEQ ID NO 14
<211> LENGTH: 20
<212> TYPE: DNA
<213> ORGANISM: Artificial Sequence
<220> FEATURE:
<223> OTHER INFORMATION: Synthetic construct

<400> SEQUENCE: 14
atagagagag tgggtgcgag                                                   20

<210> SEQ ID NO 15
<211> LENGTH: 20
<212> TYPE: DNA
<213> ORGANISM: Artificial Sequence
<220> FEATURE:
<223> OTHER INFORMATION: Synthetic construct

<400> SEQUENCE: 15
atgtagagag tgggtgcgag                                                   20

<210> SEQ ID NO 16
<211> LENGTH: 20
<212> TYPE: DNA
<213> ORGANISM: Artificial Sequence
<220> FEATURE:
<223> OTHER INFORMATION: Synthetic construct

<400> SEQUENCE: 16
atggcgagag tgggtgcgag                                                   20

<210> SEQ ID NO 17
<211> LENGTH: 20
<212> TYPE: DNA
<213> ORGANISM: Artificial Sequence
<220> FEATURE:
<223> OTHER INFORMATION: Synthetic construct

<400> SEQUENCE: 17
atggatagag tgggtgcgag                                                   20

<210> SEQ ID NO 18
<211> LENGTH: 20
<212> TYPE: DNA
<213> ORGANISM: Artificial Sequence
<220> FEATURE:
<223> OTHER INFORMATION: Synthetic construct

<400> SEQUENCE: 18
atggagggag tgggtgcgag                                                   20

<210> SEQ ID NO 19
<211> LENGTH: 20
<212> TYPE: DNA
<213> ORGANISM: Artificial Sequence
<220> FEATURE:
<223> OTHER INFORMATION: Synthetic construct

<400> SEQUENCE: 19
atggagaaag tgggtgcgag                                                   20

<210> SEQ ID NO 20
<211> LENGTH: 20
<212> TYPE: DNA
<213> ORGANISM: Artificial Sequence
<220> FEATURE:
<223> OTHER INFORMATION: Synthetic construct
```

```
<400> SEQUENCE: 20
atggagagcg tgggtgcgag                                               20

<210> SEQ ID NO 21
<211> LENGTH: 20
<212> TYPE: DNA
<213> ORGANISM: Artificial Sequence
<220> FEATURE:
<223> OTHER INFORMATION: Synthetic construct

<400> SEQUENCE: 21
atggagagat tgggtgcgag                                               20

<210> SEQ ID NO 22
<211> LENGTH: 20
<212> TYPE: DNA
<213> ORGANISM: Artificial Sequence
<220> FEATURE:
<223> OTHER INFORMATION: Synthetic construct

<400> SEQUENCE: 22
atggagagag ggggtgcgag                                               20

<210> SEQ ID NO 23
<211> LENGTH: 20
<212> TYPE: DNA
<213> ORGANISM: Artificial Sequence
<220> FEATURE:
<223> OTHER INFORMATION: Synthetic construct

<400> SEQUENCE: 23
atggagagag taggtgcgag                                               20

<210> SEQ ID NO 24
<211> LENGTH: 20
<212> TYPE: DNA
<213> ORGANISM: Artificial Sequence
<220> FEATURE:
<223> OTHER INFORMATION: Synthetic construct

<400> SEQUENCE: 24
atggagagag tgtgtgcgag                                               20

<210> SEQ ID NO 25
<211> LENGTH: 20
<212> TYPE: DNA
<213> ORGANISM: Artificial Sequence
<220> FEATURE:
<223> OTHER INFORMATION: Synthetic construct

<400> SEQUENCE: 25
atggagagag tggttgcgag                                               20

<210> SEQ ID NO 26
<211> LENGTH: 20
<212> TYPE: DNA
<213> ORGANISM: Artificial Sequence
<220> FEATURE:
<223> OTHER INFORMATION: Synthetic construct

<400> SEQUENCE: 26
atggagagag tgggagcgag                                               20

<210> SEQ ID NO 27
<211> LENGTH: 20
<212> TYPE: DNA
```

```
<213> ORGANISM: Artificial Sequence
<220> FEATURE:
<223> OTHER INFORMATION: Synthetic construct

<400> SEQUENCE: 27
atggagagag tgggttcgag                                               20

<210> SEQ ID NO 28
<211> LENGTH: 20
<212> TYPE: DNA
<213> ORGANISM: Artificial Sequence
<220> FEATURE:
<223> OTHER INFORMATION: Synthetic construct

<400> SEQUENCE: 28
atggagagag tgggtgtgag                                               20

<210> SEQ ID NO 29
<211> LENGTH: 20
<212> TYPE: DNA
<213> ORGANISM: Artificial Sequence
<220> FEATURE:
<223> OTHER INFORMATION: Synthetic construct

<400> SEQUENCE: 29
atggagagag tgggtgccag                                               20

<210> SEQ ID NO 30
<211> LENGTH: 20
<212> TYPE: DNA
<213> ORGANISM: Artificial Sequence
<220> FEATURE:
<223> OTHER INFORMATION: Synthetic construct

<400> SEQUENCE: 30
atggagagag tgggtgcggg                                               20

<210> SEQ ID NO 31
<211> LENGTH: 20
<212> TYPE: DNA
<213> ORGANISM: Artificial Sequence
<220> FEATURE:
<223> OTHER INFORMATION: Synthetic construct

<400> SEQUENCE: 31
atggagagag tgggtgcgaa                                               20

<210> SEQ ID NO 32
<211> LENGTH: 15
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(5)
<223> OTHER INFORMATION: n is a, c, g, t or u
<220> FEATURE:
<221> NAME/KEY: misc_feature
<222> LOCATION: (11)..(15)
<223> OTHER INFORMATION: n is a, c, g, t or u

<400> SEQUENCE: 32
nnnnnatagg nnnnn                                                    15

<210> SEQ ID NO 33
<211> LENGTH: 15
<212> TYPE: DNA
```

```
<213> ORGANISM: Artificial Sequence
<220> FEATURE:
<223> OTHER INFORMATION: Synthetic construct

<400> SEQUENCE: 33
tctcaactcg tagct                                                          15

<210> SEQ ID NO 34
<211> LENGTH: 15
<212> TYPE: DNA
<213> ORGANISM: Artificial Sequence
<220> FEATURE:
<223> OTHER INFORMATION: Synthetic construct

<400> SEQUENCE: 34
cgtcgcattc aggat                                                          15

<210> SEQ ID NO 35
<211> LENGTH: 42
<212> TYPE: DNA
<213> ORGANISM: Artificial Sequence
<220> FEATURE:
<223> OTHER INFORMATION: Synthetic construct

<400> SEQUENCE: 35
attgataagg attcactata ggaaagagga ttattgttaa at                            42

<210> SEQ ID NO 36
<211> LENGTH: 18
<212> TYPE: DNA
<213> ORGANISM: Artificial Sequence
<220> FEATURE:
<223> OTHER INFORMATION: Synthetic construct

<400> SEQUENCE: 36
cttatcaata tttaacaa                                                       18

<210> SEQ ID NO 37
<211> LENGTH: 18
<212> TYPE: DNA
<213> ORGANISM: Artificial Sequence
<220> FEATURE:
<223> OTHER INFORMATION: Synthetic construct

<400> SEQUENCE: 37
cttatcaata tttaacaa                                                       18

<210> SEQ ID NO 38
<211> LENGTH: 38
<212> TYPE: DNA
<213> ORGANISM: Artificial Sequence
<220> FEATURE:
<223> OTHER INFORMATION: Synthetic construct

<400> SEQUENCE: 38
ctcttcagcg atcagcaagg ctgcacccat gttagtga                                 38

<210> SEQ ID NO 39
<211> LENGTH: 30
<212> TYPE: DNA
<213> ORGANISM: Artificial Sequence
<220> FEATURE:
<223> OTHER INFORMATION: Synthetic construct

<400> SEQUENCE: 39
ctcttcagcg atcagttctt ctctctccat                                          30
```

<210> SEQ ID NO 40
<211> LENGTH: 33
<212> TYPE: DNA
<213> ORGANISM: Artificial Sequence
<220> FEATURE:
<223> OTHER INFORMATION: Synthetic construct

<400> SEQUENCE: 40
ctcgcaccca ttgaactgca cccatgttag tga                                   33

<210> SEQ ID NO 41
<211> LENGTH: 35
<212> TYPE: DNA
<213> ORGANISM: Artificial Sequence
<220> FEATURE:
<223> OTHER INFORMATION: Synthetic construct

<400> SEQUENCE: 41
ctcttcagcg atcagttctt ctctctccat gagag                                 35

<210> SEQ ID NO 42
<211> LENGTH: 38
<212> TYPE: DNA
<213> ORGANISM: Artificial Sequence
<220> FEATURE:
<223> OTHER INFORMATION: Synthetic construct

<400> SEQUENCE: 42
tgggtctcgc acccattgaa ctgcacccat gttagtga                              38

<210> SEQ ID NO 43
<211> LENGTH: 15
<212> TYPE: DNA
<213> ORGANISM: Artificial Sequence
<220> FEATURE:
<223> OTHER INFORMATION: Synthetic construct

<400> SEQUENCE: 43
gagaaggata tcact                                                       15

<210> SEQ ID NO 44
<211> LENGTH: 23
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(10)
<223> OTHER INFORMATION: n is a, c, g, t or u
<220> FEATURE:
<221> NAME/KEY: misc_feature
<222> LOCATION: (11)..(13)
<223> OTHER INFORMATION: At least one and up to three nucleotides may be
      present or absent; if present, n is a, c, g, t or u
<220> FEATURE:
<221> NAME/KEY: misc_feature
<222> LOCATION: (14)..(23)
<223> OTHER INFORMATION: n is a, c, g, t or u

<400> SEQUENCE: 44
nnnnnnnnnn nnnnnnnnnn nnn                                              23

<210> SEQ ID NO 45
<211> LENGTH: 36
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (14)..(18)
<223> OTHER INFORMATION: n is a, c, g, t or u
<220> FEATURE:
<221> NAME/KEY: misc_feature
<222> LOCATION: (19)..(21)
<223> OTHER INFORMATION: At least one and up to three nucleotides may be
      present or absent; if present, n is a, c, g, t or u
<220> FEATURE:
<221> NAME/KEY: misc_feature
<222> LOCATION: (22)..(36)
<223> OTHER INFORMATION: n is a, c, g, t or u

<400> SEQUENCE: 45
ctcttcagcg atcnnnnnnn nnnnnnnnnn nnnnnn                               36

<210> SEQ ID NO 46
<211> LENGTH: 39
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(15)
<223> OTHER INFORMATION: n is a, c, g, t or u
<220> FEATURE:
<221> NAME/KEY: misc_feature
<222> LOCATION: (16)..(18)
<223> OTHER INFORMATION: At least one and up to three nucleotides may be
      present or absent; if present, n is a, c, g, t or u
<220> FEATURE:
<221> NAME/KEY: misc_feature
<222> LOCATION: (19)..(23)
<223> OTHER INFORMATION: n is a, c, g, t or u

<400> SEQUENCE: 46
nnnnnnnnnn nnnnnnnnnn nnngcaccca tgttagtga                            39

<210> SEQ ID NO 47
<211> LENGTH: 36
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (14)..(36)
<223> OTHER INFORMATION: n is a, c, g, t or u

<400> SEQUENCE: 47
ctcttcagcg atcnnnnnnn nnnnnnnnnn nnnnnn                               36

<210> SEQ ID NO 48
<211> LENGTH: 38
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (3)..(22)
<223> OTHER INFORMATION: n is a, c, g, t or u

<400> SEQUENCE: 48
gcnnnnnnnn nnnnnnnnnn nngcacccat gttagtga                             38

<210> SEQ ID NO 49
<211> LENGTH: 31
<212> TYPE: DNA
<213> ORGANISM: Artificial Sequence
<220> FEATURE:
<223> OTHER INFORMATION: Synthetic construct

<400> SEQUENCE: 49
gtcggccctc tgcacccatg ttagtgatat a                                31

<210> SEQ ID NO 50
<211> LENGTH: 26
<212> TYPE: DNA
<213> ORGANISM: Artificial Sequence
<220> FEATURE:
<223> OTHER INFORMATION: Synthetic construct

<400> SEQUENCE: 50
ggctcttcag cgatcagagg gccgac                                      26

<210> SEQ ID NO 51
<211> LENGTH: 31
<212> TYPE: DNA
<213> ORGANISM: Artificial Sequence
<220> FEATURE:
<223> OTHER INFORMATION: Synthetic construct

<400> SEQUENCE: 51
cacgcggctc tgcacccatg ttatcactat a                                31

<210> SEQ ID NO 52
<211> LENGTH: 26
<212> TYPE: DNA
<213> ORGANISM: Artificial Sequence
<220> FEATURE:
<223> OTHER INFORMATION: Synthetic construct

<400> SEQUENCE: 52
ggaagagcag cgatcagagc cgcgtg                                      26

<210> SEQ ID NO 53
<211> LENGTH: 35
<212> TYPE: DNA
<213> ORGANISM: Artificial Sequence
<220> FEATURE:
<223> OTHER INFORMATION: Synthetic construct

<400> SEQUENCE: 53
ctcgcaccca ttgaactgca cccatgttat cacta                            35

<210> SEQ ID NO 54
<211> LENGTH: 31
<212> TYPE: DNA
<213> ORGANISM: Artificial Sequence
<220> FEATURE:
<223> OTHER INFORMATION: Synthetic construct

<400> SEQUENCE: 54
gaagagcagc gatcagttct tctctctcca t                                31

<210> SEQ ID NO 55
<211> LENGTH: 26
<212> TYPE: DNA
<213> ORGANISM: Artificial Sequence
<220> FEATURE:
<223> OTHER INFORMATION: Synthetic construct

<400> SEQUENCE: 55
cacgcggctc tgtagcgacg agaagg                                      26

<210> SEQ ID NO 56
<211> LENGTH: 31
<212> TYPE: DNA
<213> ORGANISM: Artificial Sequence
<220> FEATURE:
<223> OTHER INFORMATION: Synthetic construct

<400> SEQUENCE: 56
atatcactat tgtacccacc agagccgcgt g                              31

<210> SEQ ID NO 57
<211> LENGTH: 15
<212> TYPE: DNA
<213> ORGANISM: Artificial Sequence
<220> FEATURE:
<223> OTHER INFORMATION: Synthetic construct

<400> SEQUENCE: 57
tcactatagg aagag                                                15

<210> SEQ ID NO 58
<211> LENGTH: 26
<212> TYPE: DNA
<213> ORGANISM: Artificial Sequence
<220> FEATURE:
<223> OTHER INFORMATION: Synthetic construct

<400> SEQUENCE: 58
cgagacgcgc acccatgtta gtgata                                    26

<210> SEQ ID NO 59
<211> LENGTH: 23
<212> TYPE: DNA
<213> ORGANISM: Artificial Sequence
<220> FEATURE:
<223> OTHER INFORMATION: Synthetic construct

<400> SEQUENCE: 59
ggctcttcag cgatcgcgtc tcg                                       23

<210> SEQ ID NO 60
<211> LENGTH: 41
<212> TYPE: DNA
<213> ORGANISM: Artificial Sequence
<220> FEATURE:
<223> OTHER INFORMATION: Synthetic construct

<400> SEQUENCE: 60
ggaagaggat tattgttaaa tattgataag gattcactat a                   41

<210> SEQ ID NO 61
<211> LENGTH: 24
<212> TYPE: DNA
<213> ORGANISM: Artificial Sequence
<220> FEATURE:
<223> OTHER INFORMATION: Synthetic construct

<400> SEQUENCE: 61
aaaaaaaaaa cgtcgcattc agat                                      24

<210> SEQ ID NO 62
<211> LENGTH: 25
<212> TYPE: DNA
<213> ORGANISM: Artificial Sequence
<220> FEATURE:
<223> OTHER INFORMATION: Synthetic construct

<400> SEQUENCE: 62

```
tctcaactcg tagctaaaaa aaaaa                                          25

<210> SEQ ID NO 63
<211> LENGTH: 61
<212> TYPE: DNA
<213> ORGANISM: Artificial Sequence
<220> FEATURE:
<223> OTHER INFORMATION: Synthetic construct

<400> SEQUENCE: 63
gtaaagcact ttagttgggg aggaaagcct caaggttaat agccttgggg gaggacgtta    60
c                                                                   61

<210> SEQ ID NO 64
<211> LENGTH: 45
<212> TYPE: DNA
<213> ORGANISM: Artificial Sequence
<220> FEATURE:
<223> OTHER INFORMATION: Synthetic construct

<400> SEQUENCE: 64
ctcttcagcg atcagttctt aggctttcct ccccaactaa agtgc                    45

<210> SEQ ID NO 65
<211> LENGTH: 48
<212> TYPE: DNA
<213> ORGANISM: Artificial Sequence
<220> FEATURE:
<223> OTHER INFORMATION: Synthetic construct

<400> SEQUENCE: 65
tcctccccca aggctattaa ccttgttgaa ctgcacccat gttagtga                 48
```